United States Patent  
Kassab et al.

(10) Patent No.: US 9,681,967 B2  
(45) Date of Patent: Jun. 20, 2017

(54) LINKED DEFLECTION DEVICES, SYSTEMS AND METHODS FOR THE PREVENTION OF STROKE

(71) Applicant: CVDevices, LLC, San Diego, CA (US)

(72) Inventors: Ghassan S. Kassab, La Jolla, CA (US); Hyo Won Choi, San Diego, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 260 days.

(21) Appl. No.: 14/546,615

(22) Filed: Nov. 18, 2014

(65) Prior Publication Data

US 2015/0073533 A1  Mar. 12, 2015  
US 2016/0346103 A9  Dec. 1, 2016

Related U.S. Application Data

(63) Continuation-in-part of application No. 13/264,508, filed as application No. PCT/US2010/031475 on Apr. 16, 2010.

(Continued)

(51) Int. Cl.
*A61M 29/00* (2006.01)  
*A61F 2/90* (2013.01)

(Continued)

(52) U.S. Cl.
CPC .................. *A61F 2/90* (2013.01); *A61F 2/01* (2013.01); *A61F 2/89* (2013.01); *A61F 2/95* (2013.01);

(Continued)

(58) Field of Classification Search
CPC .... A61F 2/82; A61F 2/852; A61F 2/89; A61F 2/90; A61F 2/95; A61F 2/954;

(Continued)

(56) References Cited

U.S. PATENT DOCUMENTS 5,332,402 A   7/1994 Teitelbaum  
5,935,139 A   8/1999 Bates  
(Continued)

FOREIGN PATENT DOCUMENTS

JP   1221155   9/1989

OTHER PUBLICATIONS

International Searching Authority, International Search Report, dated Jun. 15, 2010 (PCT/US10/31475).

(Continued)

*Primary Examiner* — Robert Lynch  
(74) *Attorney, Agent, or Firm* — Reichel Stohry LLP; Mark C. Reichel; Natalie J. Dean

(57) ABSTRACT

Devices, systems, and methods for the prevention of stroke. Devices and systems hereof comprise stents configured to fit within at least part of an artery extending from an aortic arch, and at least one component comprising parallel convex struts for diverting emboli from entering an artery when the component is positioned at or near its ostium. The stents and the deflection component(s) are coupled in a linked configuration. Additionally, a retrieval system is provided, the retrieval system comprising a sleeve catheter and a retrieval device slidably disposed therein. The distal end of the retrieval device comprises an attachment portion configured to engage a device positioned within an artery extending from the aortic arch.

20 Claims, 15 Drawing Sheets

Related U.S. Application Data

(60) Provisional application No. 61/905,523, filed on Nov. 18, 2013, provisional application No. 61/169,767, filed on Apr. 16, 2009.

(51) Int. Cl.
| | | |
|---|---|---|
| *A61F 2/01* | (2006.01) | |
| *A61F 2/89* | (2013.01) | |
| *A61F 2/966* | (2013.01) | |
| *A61F 2/82* | (2013.01) | |
| *A61F 2/954* | (2013.01) | |
| *A61F 2/962* | (2013.01) | |
| *A61F 2/848* | (2013.01) | |
| *A61F 2/95* | (2013.01) | |

(52) U.S. Cl.
CPC ............... *A61F 2/966* (2013.01); *A61F 2/82* (2013.01); *A61F 2/954* (2013.01); *A61F 2/962* (2013.01); *A61F 2002/011* (2013.01); *A61F 2002/016* (2013.01); *A61F 2002/821* (2013.01); *A61F 2002/828* (2013.01); *A61F 2002/8486* (2013.01); *A61F 2002/9528* (2013.01); *A61F 2230/0067* (2013.01); *A61F 2230/0091* (2013.01); *A61F 2250/0098* (2013.01)

(58) Field of Classification Search
CPC .... A61F 2/962; A61F 2/966; A61F 2002/061; A61F 2002/828; A61F 2002/9505; A61F 2002/9511; A61F 2002/9528; A61F 2002/9534; A61F 2002/9665
See application file for complete search history.

(56) References Cited

U.S. PATENT DOCUMENTS

| | | |
|---|---|---|
| 5,944,738 A | 8/1999 | Amplatz et al. |
| 6,096,071 A | 8/2000 | Yadav |
| 6,309,399 B1 | 10/2001 | Barbut et al. |
| 6,361,545 B1 | 3/2002 | Macoviak et al. |
| 6,499,487 B1 | 12/2002 | McKenzie et al. |
| 6,682,543 B2 | 1/2004 | Barbut et al. |
| 6,695,858 B1 | 2/2004 | Dubrul et al. |
| 6,740,112 B2 | 5/2004 | Yodfat et al. |
| 7,244,267 B2 | 7/2007 | Huter et al. |
| 7,367,985 B2 | 5/2008 | Mazzocchi et al. |
| 7,455,688 B2 | 11/2008 | Furst et al. |
| 7,479,153 B2 | 1/2009 | Belef |
| 7,493,162 B2 | 2/2009 | Girouard et al. |
| 7,537,600 B2 | 5/2009 | Eskuri |
| 2003/0158574 A1 | 8/2003 | Esch et al. |
| 2004/0064092 A1 | 4/2004 | Tsugita et al. |
| 2005/0159773 A1 | 7/2005 | Broome et al. |
| 2005/0267516 A1 | 12/2005 | Soleimani et al. |
| 2006/0015138 A1 | 1/2006 | Gertner |
| 2007/0179592 A1 | 8/2007 | Schaeffer |
| 2007/0208410 A1 | 9/2007 | Berra et al. |
| 2008/0140110 A1 | 6/2008 | Spence |
| 2008/0255603 A1 | 10/2008 | Naor et al. |
| 2009/0099647 A1 | 4/2009 | Glimsdale et al. |
| 2009/0254172 A1 | 10/2009 | Grewe |
| 2012/0041471 A1* | 2/2012 | Kassab ............... A61F 2/90 606/200 |
| 2013/0131714 A1* | 5/2013 | Wang ............... A61F 2/01 606/200 |

OTHER PUBLICATIONS

International Searching Authority, Written Opinion of the International Searching Authority, dated Jun. 15, 2010 (PCT/US10/31475).

\* cited by examiner

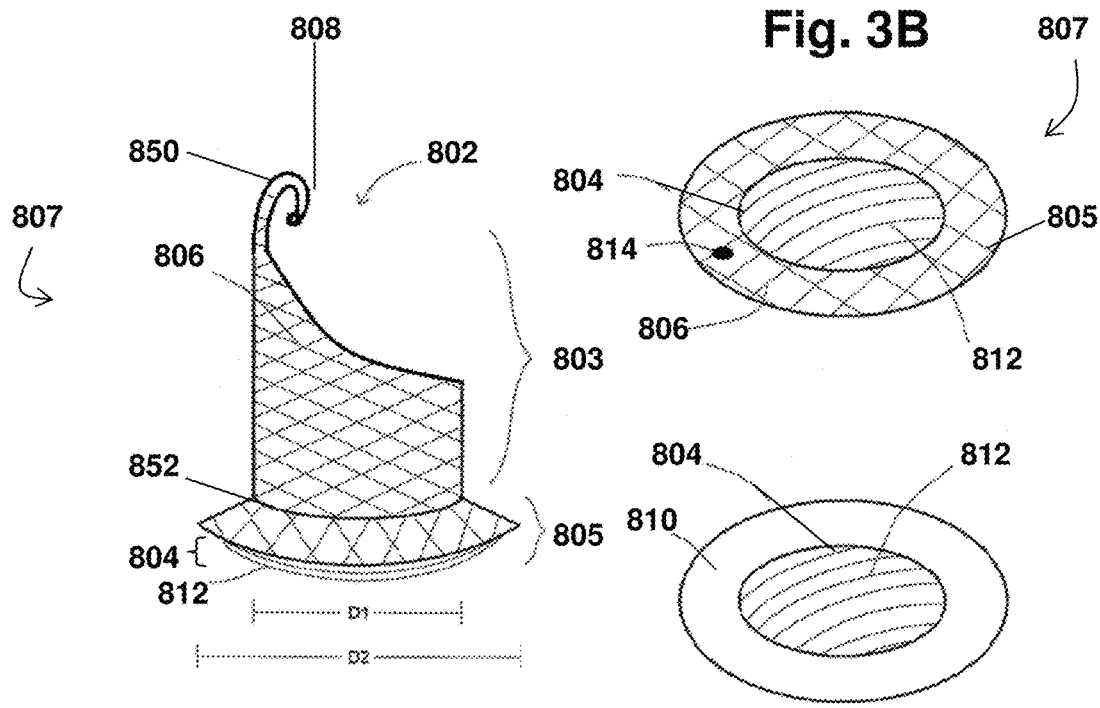
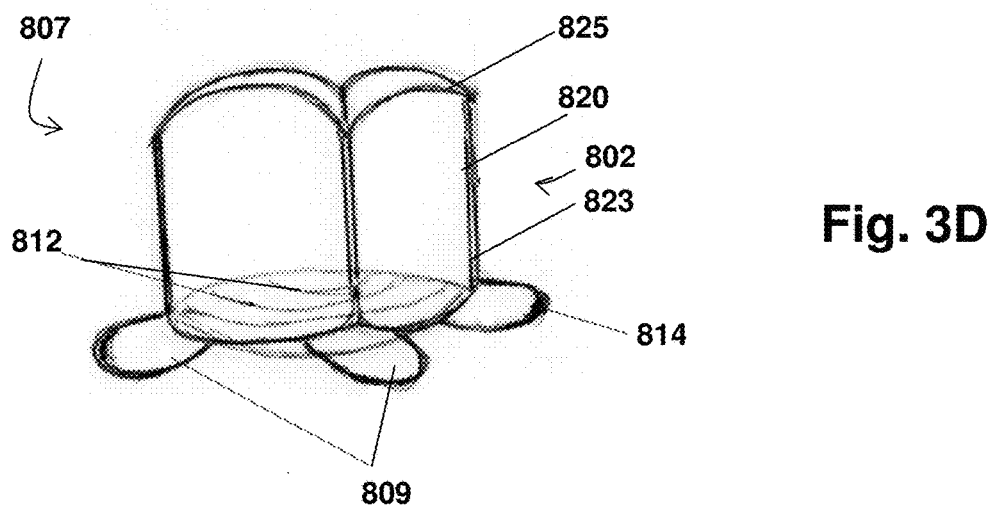

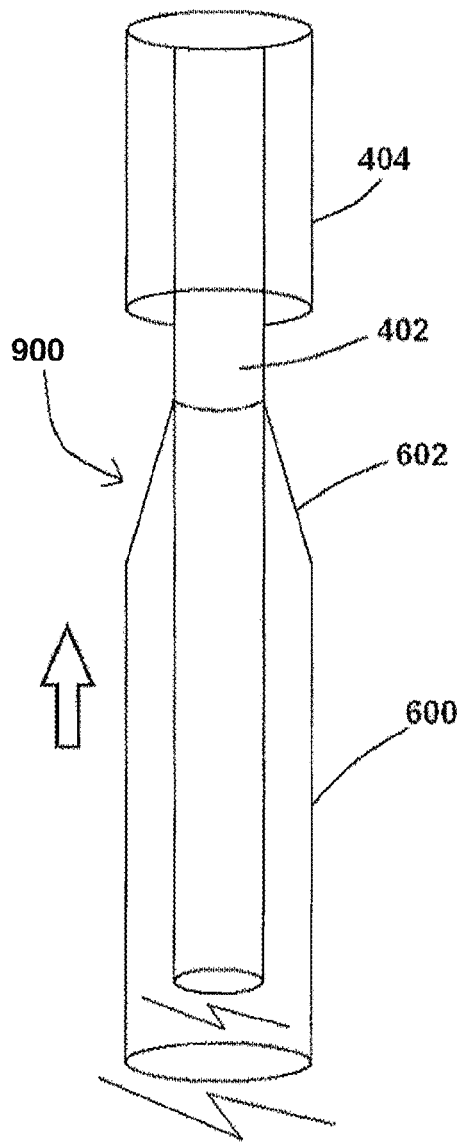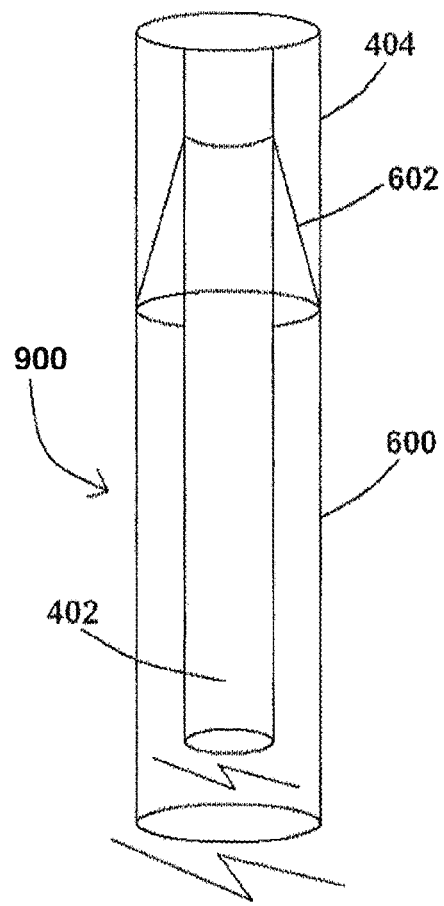
Fig. 9A
Fig. 9B

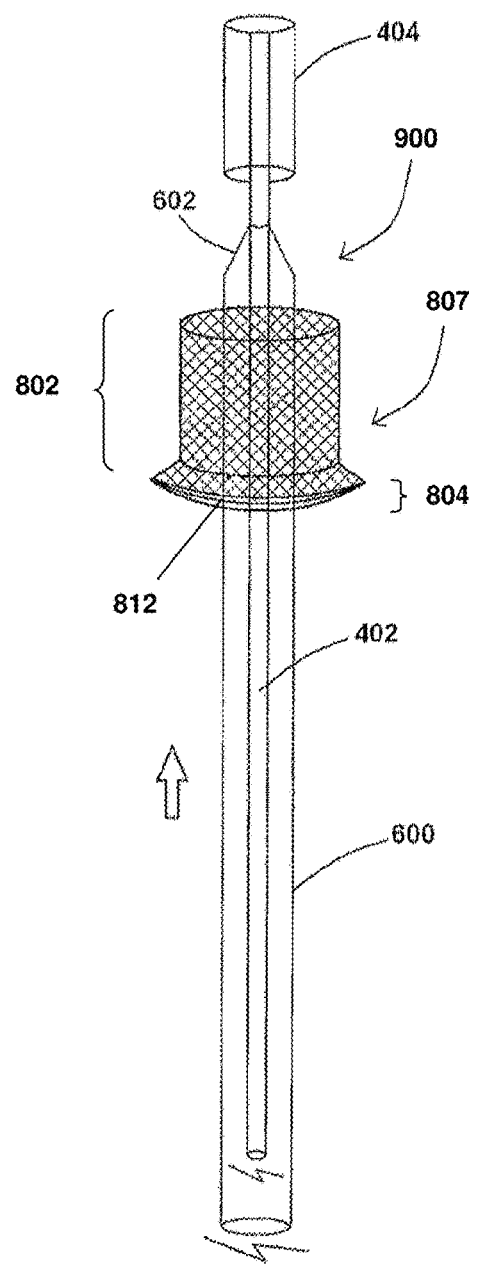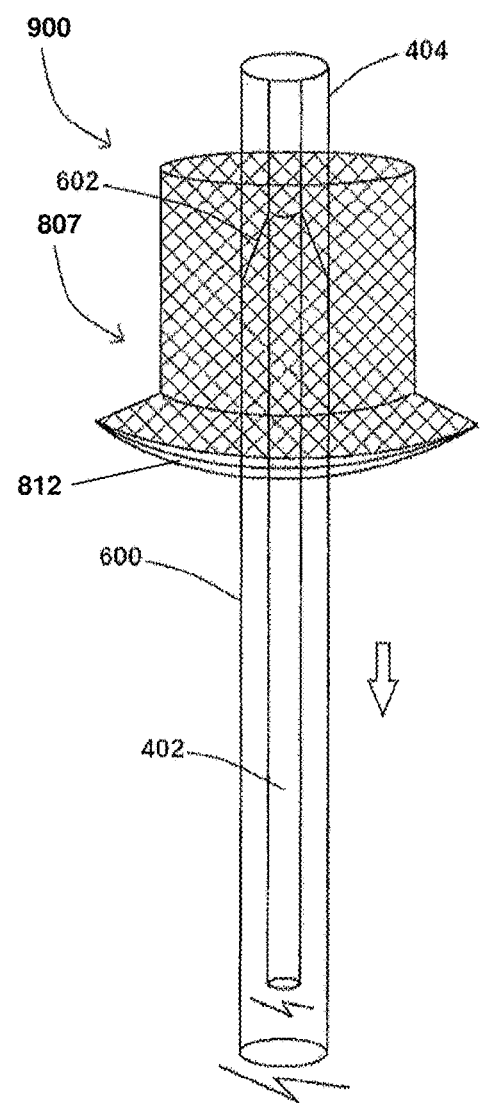
Fig. 10A
Fig. 10B

LINKED DEFLECTION DEVICES, SYSTEMS AND METHODS FOR THE PREVENTION OF STROKE

PRIORITY

This application (a) is related to, and claims the priority benefit of, U.S. Provisional Patent Application Ser. No. 61/905,523, filed Nov. 18, 2013, and (b) is related to, claims the priority benefit of, and is a U.S. continuation-in-part application of, U.S. patent application Ser. No. 13/264,508, filed Oct. 14, 2011, which is related to, and claims the priority benefit of, International Application Serial No. PCT/US10/31475, filed Apr. 16, 2010, which is related to, and claims the priority benefit of, U.S. Provisional Patent Application Ser. No. 61/169,767, filed Apr. 16, 2009. The entire contents of the aforementioned priority and related applications are hereby incorporated by reference in their entirety into this disclosure.

BACKGROUND

Stroke

A stroke, or cerebrovascular accident as otherwise known, is defined as a rapidly developing loss of brain function due to a disturbance in the blood supply to the brain. This can be due to ischemia (lack of blood supply) caused by thrombosis or embolism or due to a hemorrhage. As a result, the affected area of the brain is unable to function, leading to the inability to move one or more limbs on one side of the body, the inability to understand or formulate speech, or the inability to see one side of the visual field amongst others.

Each year, about 800,000 people experience a new or recurrent stroke. Approximately 600,000 of these are first attacks, and 200,000 are recurrent attacks. In addition, and on average, someone in the U.S. has a stroke every 40 seconds, and each year about 55,000 more women than men have a stroke. On average, every 3-4 minutes, someone dies of a stroke. Because women live longer than men, more women than men die of stroke each year. Women accounted for 60.6% of U.S. stroke deaths in 2005. Men stroke incidence rates are greater than women at younger ages but not at older ages. Despite advances in stroke prevention treatments, the incidence of hospitalized stroke and case fatality did not decrease. African-Americans have almost twice the risk of first-ever stroke than whites. The age adjusted stroke incidence rates in people 45-84 years of age are 6.6 per 1000 population in black men, 3.6 in white men, 4.9 in black women, and 2.3 in white women.

Of all strokes, 87% are ischemic, 10% are intracerebral hemorrhage, and 3% are subarachnoid hemorrhage strokes. Stroke accounted for about 1 out of every 17 deaths in the U.S. in 2005, and approximately 53% of stroke deaths in 2005 occurred out of the hospital.

Total stroke mortality in 2005 was about 150,000. The 2005 overall death rate for stroke was 46.6 per 100,000. Death rates were 44.7 for white males, 70.5 for black males, 44.0 for white females, and 60.7 for black females, all per 100,000. When considered separately from other cardiovascular diseases, stroke ranks no. 3 among all causes of death, behind heart disease and cancer. Moreover, stroke is the leading cause of serious, long-term disability in the United States. Indeed, it is widely recognized that strokes are a major cause of adult disability due to both the debilitating initial symptoms and in many cases severe long-term impairment.

A report released by the Centers for Disease Control (CDC) in collaboration with the Centers for Medicare and Medicaid Services (CMS), the Atlas of Stroke Hospitalizations Among Medicare Beneficiaries, found that in Medicare beneficiaries, 30-day mortality rate varied by age: 9% in patients 65 to 74 years of age, 13.1% in those 74 to 84 years of age, and 23% in those 85 years of age. Accordingly, it is clear that prevalence of stroke is associated with substantial health, quality of life and economic costs.

Atrial Fibrillation

Atrial fibrillation (AF) is a significant, independent risk factor for ischemic stroke, increasing risk about 5-fold. The percentage of strokes attributable to AF increases steeply from 1.5% at 50 to 59 years of age to 23.5% at 80 to 89 years of age. Most strokes in patients with AF are cardioembolic caused by embolism of left atrial appendage thrombi, but some are caused by coexisting intrinsic cerebrovascular diseases in typically elderly, often hypertensive patients.

AF carries an annual risk of thromboembolic complications of 3-6%, which is 5-7 times greater than that of controls with sinus rhythm. AF is present in 15-21% of patients affected by stroke. AF/flutter, a strong risk factor for stroke, is arguably the most important finding on cardiac workup in patients with ischemic stroke. Once identified, introduction of oral anticoagulant therapy (warfarin, for example) provides a 40% risk reduction in recurrent stroke compared with antiplatelet therapy. Ischemic stroke with AF is associated with greater disability and mortality than those without AF. However, not all patients can receive anticoagulant or antiplatelet therapies, and the same or other patients may be prone to clots that form in the left atrial appendage and enter the bloodstream, so other types of therapies would be required.

Patients with AF have an increased risk of major, disabling stroke, often caused by large infarctions in the middle cerebral artery territory. Some studies showed that AF was associated with an increased risk of death in the first four weeks after stroke likely due to the advanced age in stroke patients with AF, large infarction, severe neurological deficits, and poor functional outcomes.

First, strokes in patients with AF may largely be cardioembolic, which causes a sudden occlusion of large cerebral arteries without sufficient collateral blood flow, resulting in more severe strokes. Several studies have reported that stroke patients with AF often have large cortical infarcts on computed tomography, and less frequently have lacunar infarction as compared with patients without AF.

Heart Failure

Patients with heart failure (HF) are at increased risk for thromboembolic events. Left ventricular (LV) thrombus provides a substrate for events and a rationale for anticoagulation. Echocardiography studies have yielded conflicting results, however, regarding thrombus prevalence. Among populations with similar degrees of systolic dysfunction, studies have reported over a 20-fold difference in prevalence, ranging from 2.1% to 50%. Moreover, when thrombus is identified, conflicting findings have been reported concerning the risk of future embolic events.

The impact of nonrheumatic atrial fibrillation, hypertension, coronary heart disease, and cardiac failure on stroke incidence was examined in the Framingham Study. Compared with subjects free of these conditions, the age-adjusted incidence of stroke was more than doubled in the presence of coronary heart disease and more than tripled in the presence of hypertension. There was a more than fourfold excess of stroke in subjects with HF and nearly fivefold increase when atrial fibrillation was present. In persons with coronary heart disease or HF, atrial fibrillation doubled the stroke risk in men and tripled the risk in women. Factors that predispose to thromboembolic events in patients with HF include low cardiac output, with relative stasis of blood in dilated cardiac chambers, poor contractility and regional wall motion abnormalities and concomitant atrial fibrillation.

BRIEF SUMMARY

In at least one exemplary embodiment of a device for the prevention of stroke of the present disclosure, the device comprises at least two stents and at least one deflection component coupled to at least one of the stents by one or more connecting wires. Each of the stents of the device comprises an extension portion having a first end and a second end and is sized and shaped to fit within at least part of an artery extending from an aortic arch. Further, the at least one deflection component comprises a frame and two or more parallel convex struts. The frame of each deflection component defines an interior that is substantially the same size or larger than an ostium of an artery extending from the aortic arch and the two or more parallel convex struts positioned across such interior are configured to divert an embolus from entering the artery when the deflection component is positioned at or near the ostium of the artery.

In another embodiment, the two or more parallel convex struts comprise four or more parallel convex struts. In an exemplary embodiment, when the device is positioned within the artery extending from an aortic arch, the two or more parallel convex struts are positioned in an orientation that is either approximately perpendicular to, or in a direction of (i.e. approximately parallel with), or in an oblique manner relative to, blood flow within the aortic arch. In an additional embodiment, the device comprises a stent. In yet an additional embodiment, the at least two stents are autoexpandable from a collapsed configuration to an expanded configuration.

In at least one exemplary embodiment of a device for the prevention of stroke of the present disclosure, the device comprises a first stent, a second stent, a first deflection component and a second deflection component. In this embodiment, the frame of the first deflection component comprises the second end of the extension portion of the first stent and the interior of the first deflection component comprises an opening defined within the second end of the extension portion of the first stent. Furthermore, the second deflection component is coupled with the first deflection component and the second stent by one or more connecting wires thereby forming a linked configuration.

In yet another exemplary embodiment, the device again comprises a first stent, a second stent, a first deflection component and a second deflection component; however, the first deflection component is coupled with the first stent and the second deflection component by the one or more connecting wires, and the second deflection component is coupled with the second stent by one or more connecting wires. Alternatively, the device may further comprise a unit comprising a first deflection component and a second deflection component. In this at least one embodiment, the unit is configured to conform to the curvature of the aortic arch and is coupled with a first stent and a second stent by one or more connecting wires.

In at least one exemplary embodiment of a device for the prevention of stroke of the present disclosure, the extension portion comprises a substantially cylindrical shape. In another embodiment, the extension portion comprises an extension mesh comprising multiple wires. In yet another embodiment, the extension portion has a length between about 1.5 cm to about 2.5 cm. In an additional embodiment, the extension portion has a diameter between about 6 mm to about 8 mm when the extension portion is in an expanded configuration. In yet an additional embodiment, the extension portion has a diameter between about 1.8 mm to about 2.0 mm when the extension portion is in a compressed configuration.

In at least one exemplary embodiment of a device for the prevention of stroke of the present disclosure, the device is comprised of a material selected from the group consisting of stainless steel, cobalt-chromium-nickel-molybdenum-iron alloy, tantalum, nitinol, nickel-titanium, polymer materials, and a shape-memory polymer. Furthermore, in at least one embodiment, the at least two stents of the device are both autoexpandable from a collapsed configuration to an expanded configuration and the first end of the extension portion of each of the at least two stents further comprises a tip connector configured to facilitate moving each stent from the expanded configuration to the collapsed configuration.

In at least one exemplary embodiment of a device for the prevention of stroke of the present disclosure, the device further comprises one or more radiopaque markers positioned thereon. In at least one exemplary embodiment of a device for the prevention of stroke of the present disclosure, the diameter of each of the two or more parallel convex struts is between about 0.25 mm and about 1.0 mm, inclusive. In another embodiment, the two or more parallel convex struts are positioned between about 0.75 mm to about 1.0 mm, inclusive, from one another. In yet another embodiment, the two or more parallel convex struts are flexible. In yet additional embodiments, at least one of the one or more connecting wires comprise springs.

Other embodiments of the device disclosed herein may comprise one or more stents of the device further comprising an anchor portion coupled with the second end of the extension portion of such stent. In this embodiment, the anchor portion is sized and shaped to prevent the stent from advancing into the artery extending from the aortic arch in which the extension portion may be at least partially positioned. In still further embodiments, the anchor portion of at least one of the stents of the device comprises either a flange portion or two or more wings.

In at least one exemplary embodiment of a retrieval system for the prevention of stroke of the present disclosure, the system comprises a device for the prevention of stroke, a sleeve catheter and a retrieval device. The device may comprise any of the embodiments described herein, but in at least one embodiment comprises at least two stents and at least one deflection component, where at least one of the stents is coupled with at least one deflection component by one or more wires. There, each stent of the device comprises an extension portion having a first end and a second end, and the extension portion is sized and shaped to fit within at least part of an artery extending from an aortic arch and the first end of at least one of the extension portions of the stents comprising a tip connector. Furthermore, the deflection component comprises a frame and two or more parallel convex struts. The frame of the deflection component defines an interior substantially the same size or larger than an ostium of an artery extending from the aortic arch, and the two or more parallel convex struts positioned across the interior are configured to divert an embolus from entering the artery when the deflection component is positioned at or near the ostium of the artery. As previously noted, the retrieval system further comprises a sleeve catheter and a retrieval device. The sleeve catheter is configured for intravascular insertion and advancement, and comprises a proximal end, an open distal end, and a lumen extending therebetween. The retrieval device is slidably disposed within the lumen of the sleeve catheter, and comprises a proximal end for manipulation by a user and a distal end comprising an attachment portion configured to engage the tip connector of at least one of the extension portions of the stents.

In at least one embodiment of the retrieval system, the device comprises a first stent, a second stent, a first deflection component and a second deflection component. The frame of the first deflection component comprises the second end of the extension portion of the first stent and the interior of the frame of the first deflection component comprises an opening defined within the second end of the extension portion of the first stent. Furthermore, in this at least one embodiment, the second deflection component is coupled with the first deflection component and the second stent by one or more connecting wires. In yet another embodiment of the retrieval system for the prevention of stroke disclosed herein, the tip connector of at least one of the extension portions of the stents comprises a screw tip and a first magnet and the attachment portion of the retrieval device comprises a screw hole and a second magnet. Furthermore, the screw tip and the first magnet are configured to securely engage the screw hole and the second magnet, respectively. Alternatively, the attachment portion of the retrieval device may comprise a lace component and the tip connector of the at least one extension portion of the stents may comprise a hook tip configured to engage the lace component of the retrieval device.

In at least one exemplary embodiment of a method for preventing stroke of the present disclosure, the method comprises the steps of introducing a device for preventing stroke of the present disclosure into a body; navigating the device within the body until the device reaches an aortic arch; positioning a first stent within a first vessel branching from the aortic arch so that each of the at least one deflection components of the device substantially covers an ostium of a vessel branching from the aortic arch; anchoring the first stent within the first vessel by deploying the extension portion of the stent; positioning a second stent within a second vessel branching from the aortic arch; and anchoring the second stent within the second vessel by deploying the extension portion of the second stent. In another embodiment, the method further comprises the steps of introducing a retrieval system into a body, the retrieval system comprising a sleeve catheter and a retrieval device, the sleeve catheter configured for intravascular insertion and advancement; navigating the sleeve catheter within the body until an open distal end of the sleeve catheter reaches the second vessel branching from the aortic arch; advancing a distal end of the retrieval catheter through the open distal end of the sleeve catheter so that an attachment portion of the retrieval catheter engages a tip connector on the first end of the extension portion of the second stent; disengaging the second stent from the second vessel; disengaging the first stent from the first vessel; and withdrawing the device and the retrieval system from the body. In yet another embodiment of the method, the sleeve catheter of the retrieval system comprises a proximal end, an open distal end, and a lumen extending therebetween, and the retrieval device is slidably disposed within the lumen of the sleeve catheter. Here, the retrieval device of the retrieval system may further comprise a proximal end for manipulation by a user and a distal end comprising one or more attachment portions, each of which is configured to engage the a tip connector an extension portion of at least one of the devices positioned within a body.

BRIEF DESCRIPTION OF THE DRAWINGS

FIG. 3A shows an embodiment of a deflection stent of the device comprising a planar flange, according to the present disclosure;

FIGS. 3B and 3C show bottom views of embodiments of a device comprising a planar flange, according to the present disclosure;

FIG. 3D shows a side view of an embodiment of a device for the prevention of stroke comprising a stent frame and two or more wings according to the present disclosure;

FIGS. 9A and 9B show at least a portion of an exemplary system for preventing stroke, said system comprising a conical dilator useful to facilitate removal of at least a portion of the exemplary system from the body, according to the present disclosure;

FIGS. 10A and 10B show additional embodiments of an exemplary system for preventing stroke, according to the present disclosure;

Figure 1:
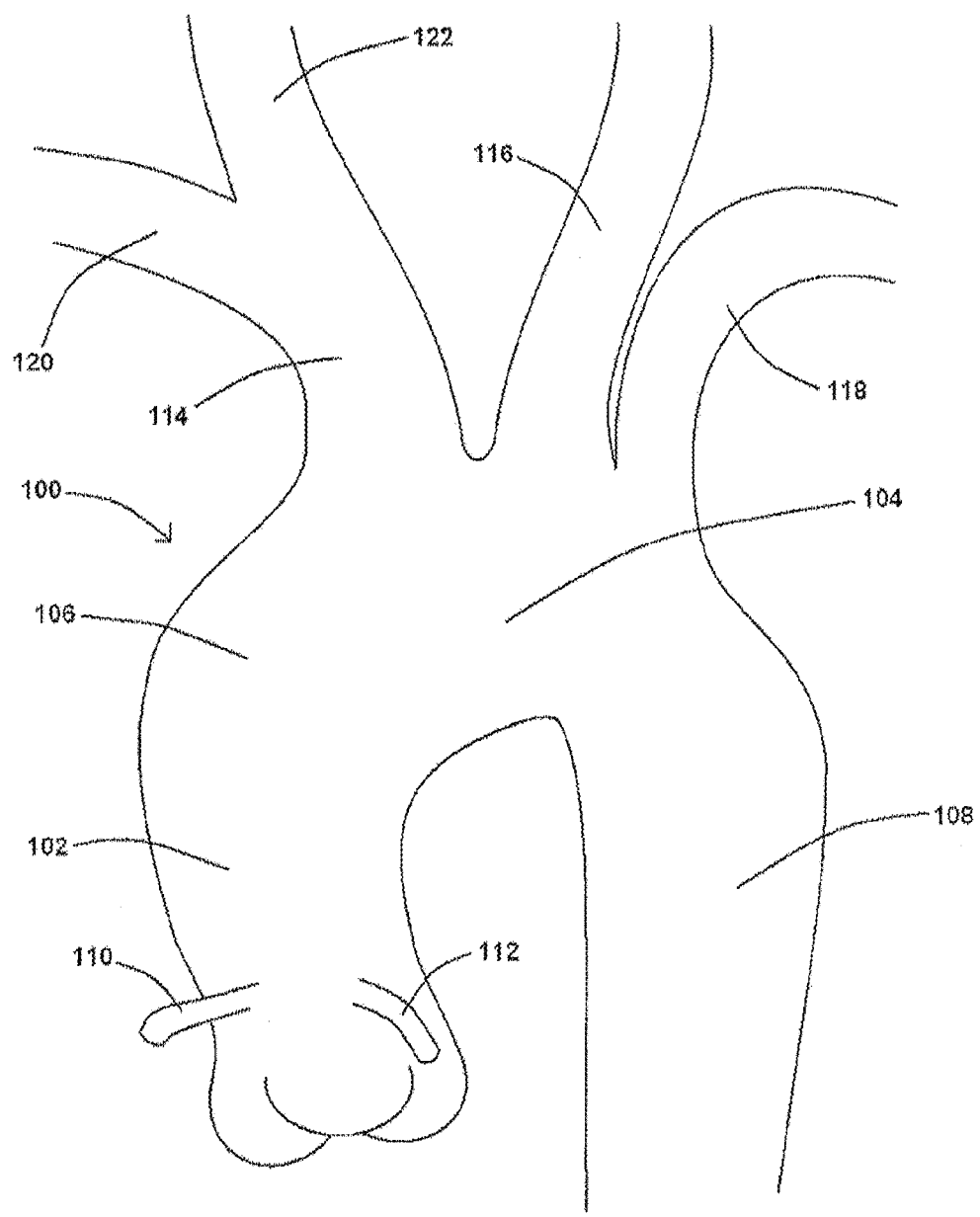
FIG. 1 shows a diagram of at least a portion of an aorta, according to the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as other discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. Furthermore, numerous specific details are set forth in order to provide a thorough understanding of the present disclosure. Particular examples may be implemented without some or all of these specific details. In other instances, well known devices or processes have not been described in detail so as to not unnecessarily obscure the present disclosure.

Various devices, systems, methods and techniques of the present disclosure will sometimes describe a connection between two components. Words such as attached, affixed, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted. Furthermore, wherever feasible and convenient, like reference numerals are used in the figures and the description to refer to the same or like parts or steps. Additionally, the drawings are in a simplified form and not to precise scale.

The disclosure of the present application provides various devices, systems, and methods for the prevention of stroke. The devices, systems, and methods disclosed herein facilitate stroke prevention, in part, by addressing specific areas of the heart and diverting the trajectories of blood clots away therefrom. Such devices, systems and methods have minimal to no influence on resistance of blood flow through the targeted areas and do not significantly affect upstream blood flow patterns. Accordingly, the devices, systems and methods disclosed herein protect against stroke without significantly affecting proper perfusion of the protected arterial territories.

A diagram of at least a portion of an exemplary aorta is shown in FIG. 1. An aorta 100 is the main trunk of a vascular system which conveys oxygenated blood to the tissues of a body. It begins at the upper part of the left ventricle, where it may be approximately 3 cm in diameter in an adult human. As shown in FIG. 1, and at the union of the ascending aorta 102 with the aortic arch 104 (or the "arch of aorta"), the caliber of the vessel is increased, owing to a bulging of its right wall. This dilatation is termed the aortic bulb 106 (or bulb of the aorta), and on transverse section shows a somewhat oval figure. The ascending aorta 102 is contained within the pericardium and is enclosed in a tube of the serous pericardium. It ascends for a short distance (the ascending aorta 102 is about 5 cm in length in an adult human), arches backward, and then descends within the thorax and abdomen (the descending aorta 108) and ends into the right and left common iliac arteries (about 1.7 cm in diameter in an adult human). The right coronary 110 and the left coronary 112, as shown in FIG. 1, branch from the ascending aorta 102.

There are three arteries that branch from the aortic arch 104, namely the innominate artery 114, the left common carotid artery 116, and the left subclavian artery 118. Instead of arising from the highest part of the aortic arch 104, these branches may spring from the commencement of the aortic arch 104 or the upper part of the ascending aorta 102. The distance between the aortic arch 104 or the upper part of the ascending aorta 102 at their origins may be increased or diminished, the most frequent variation being the approximation of the left common carotid artery 116 toward the innominate artery 114. In addition, and as shown in FIG. 1, the innominate artery 114 branches into the right subclavian artery 120 and the right common carotid artery 122.

Ischemic strokes, the most common type of stroke, occur when blood clots or other debris are swept through the bloodstream and lodge in one or more of the aortic branches 114, 116. As the innominate and left common carotid arteries 114, 116 ultimately supply blood to the brain, the partial or complete blockage thereof reduces or inhibits blood flow to the brain, thus increasing the risk of ischemic stroke. Ejection dynamics of blood clots from the left ventricle are diverse and random, with clots having different release velocities at different stages of the cardiac cycle. Furthermore, blood clots can vary in size—typically in the range of about 2 mm to about 6 mm—which can also have a significant effect on clot velocity and their flow patterns as they leave the heart. In addition, the hemodynamics in the aortic arch 104 is typically characterized as complex flow patterns due to the arch curvature and branches 114, 116. Accordingly, clot trajectory is a complex function of aortic flow conditions, discrete phase behavior of clots, and their dynamic interactions. To prevent ischemic stroke, not only must clots be prevented from lodging within the aortic branches 114, 116, but the solution must be mindful of the complexity of the aortic flow field, not generate a substantial resistance to flow therethrough, and take steps to reduce the likelihood of downstream thrombosis formation.

The devices, systems, and methods of the present application are configured to maintain a balance between efficacy in deflecting blood clots from an artery extending from the aortic arch 104 and affecting minimal influence on the high-risk supra-aortic arterial structures of the aorta 100 and the resistance to blood flow therethrough. In this manner, such deflection devices, systems and methods can ensure diversion of blood clots away from the aortic branches 114, 116, rather than blocking clots on the device and thereby obstructing the underlying arteries.

Figure 2A:
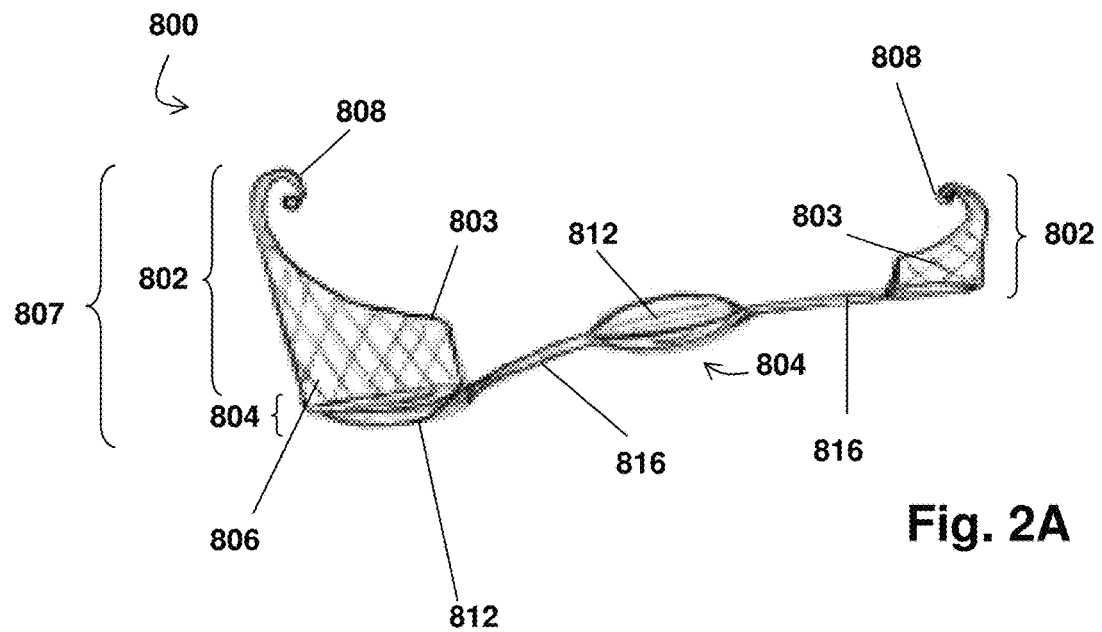
FIGS. 2A and 2B show exemplary embodiments of a device for the prevention of stroke, according to the present disclosure.
Figure 2B:
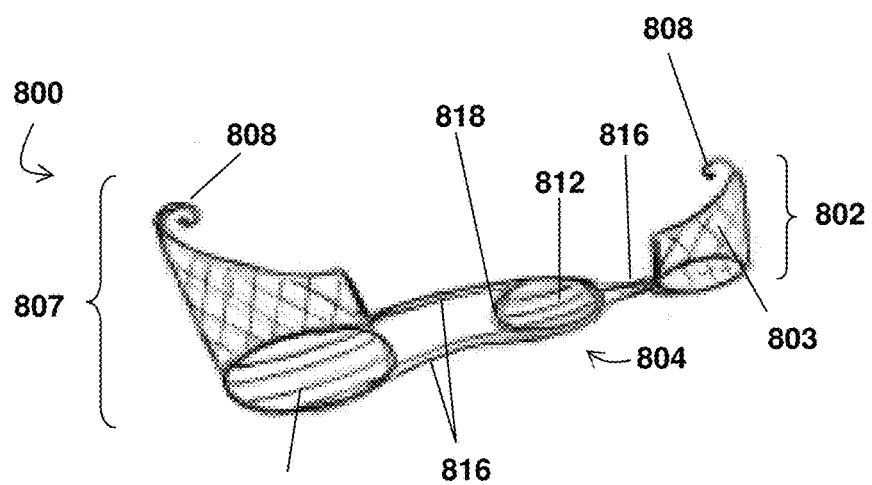

FIGS. 2A and 2B show exemplary embodiments of a device of the present application for the prevention of stroke. In application, such device (and any embodiments thereof) may be used with one or more of the aortic branches 114, 116, 118 to deflect the trajectory of blood clots destined for high-risk structures of the aorta 100 with negligible change in blood flow resistance.

As shown in FIG. 2A, an exemplary device 800 comprises a device having at least two stents 802 and at least one deflection component 804 connected by one or more connecting wires 816 extending therebetween. This device 800 is configured for placement within the aortic arch 104 such that the stents 802 are each positioned within a supra-aortic arterial branch to anchor the device 800, and the deflection component(s) 804 traverse the ostium of at least a portion of a supra-aortic arterial branch 114, 116, 118 to prevent blood clots from entering the same. Furthermore, the device 800 (or independent components thereof) may be collapsible and/or autoexpandable to facilitate delivery, secure anchoring, and/or the long term stability of the device 800 after placement. As such, in this at least one embodiment, the device 800 can be easily folded, sheathed and loaded into a delivery tool, thereby facilitating ease of delivery and placement of the device 800 within a patient.

The connecting wire(s) 816 of the device 800 are sufficiently flexible so as to accommodate the shape of an aortic arch 104, yet, in at least one embodiment, incompliant enough to provide the device 800 some degree of structure and support. Moreover, the length of the connecting wires 816 between the stents 802 and/or deflection component(s) 804 may be adjusted depending on where in the supra-aortic arterial branches the device 800 is to be anchored and/or to accommodate the frequent anatomic variations of the aortic arch 104 anatomy between patients. As such, the precise distance between the stents 802 and deflection component(s) 804 of the device 800 varies and may be customized for each patient, application, or even standardized for different classes of patients.

Figure 2C:
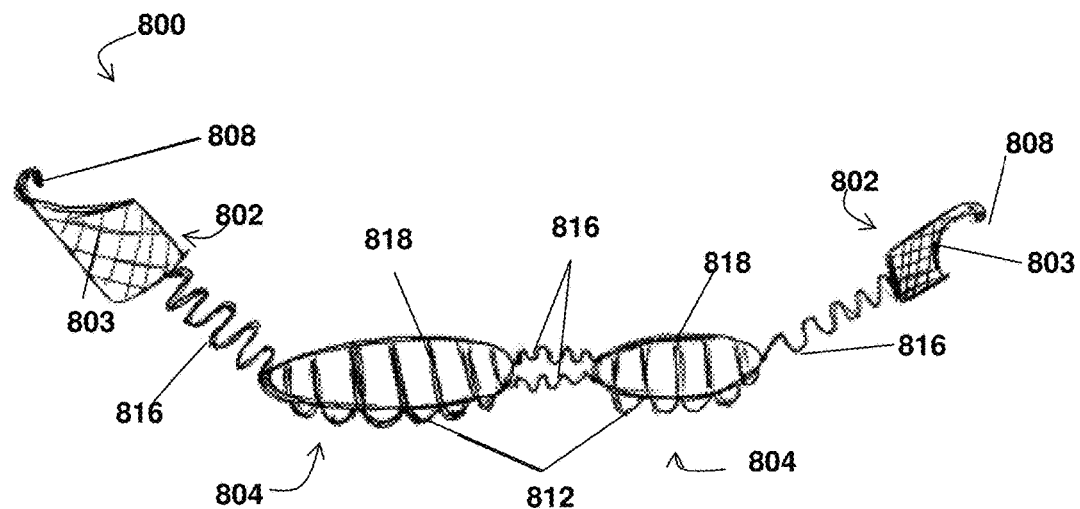
FIGS. 2C and 2D show exemplary embodiments of the device of FIGS. 2A and 2B where the connecting wire(s) thereof comprise springs.
Figure 2D:
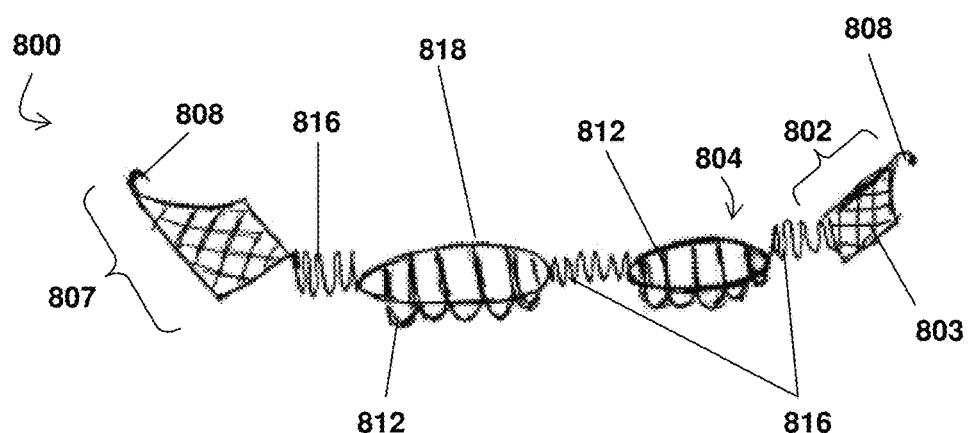

Additionally or alternatively, the connecting wire(s) 816 may comprise a spring configuration, an example of which is shown in FIGS. 2C and 2D. In this at least one embodiment, the length of the overall device 800 and/or the distances between each component thereof may be modified in situ. For example, during the course of positioning and deploying the device 800, a clinician can extend or compress one or more of the connecting wire(s) 816 (or a portion thereof) to properly position the device 800 within the targeted structures and the aortic arch 104. FIG. 2C illustrates such a device 800 with the connecting wire(s) 816 in an extended configuration and FIG. 2D illustrates the same device 800 with the connecting wire(s) 816 in a compressed configuration. While FIGS. 2C and 2D show the totality of the connecting wire(s) 816 at relatively the same degree of extension or compression, respectively, it will be appreciated that different portions of the connecting wire(s) 816 may be extended or compressed individually to accommodate different anatomies (e.g., the connecting wire 816 connecting the deflection stent 807 (described below) and a deflection component 804 may be in an extended configuration while the connecting wire 816 connecting a deflection component 804 and the stent 802 is in a compressed state). Accordingly, the spring configuration of the connecting wire(s) 816 enables a standard-sized device 800 to be precisely fit to a patient, irrespective of anatomical variations in aortic arch anatomy.

FIGS. 3A-3D illustrate at least some embodiments of several of the components of the device 800. Each stent 802 comprises an extension portion 803, which may be a cylindrical stent sized and shaped to fit securely within an aortic branch. Additionally, as shown in FIGS. 2A and 2B, the distal-most part of the extension portion 803 may further comprise an angular opening having a tip connector 808 extending therefrom. The tip connector 808 can comprise any configuration operable to removably engage a delivery device and will be discussed in further detail below. For example, in the embodiments shown in FIGS. 2A-3A, the tip connector 808 comprises a hook.

An exemplary extension portion 803 may comprise, for example, mesh 806 having multiple wires as shown in FIGS. 2A-3C. The extension portion 803 may alternatively comprise a stent frame 820 without the inclusion of mesh 806 or other materials thereon as shown in FIG. 3D. Exemplary stent frames 820, such as shown in FIG. 3D, may comprise a plurality of extension struts 823 positioned around a relative perimeter or circumference of deflection stent 807 (such as around the opening where convex struts 812 are located), extending from second end 852 toward first end 850, and may be connected to one another using one or more connection struts 825, which may be curved as desired as shown in FIG. 3D. In this embodiment of the device 800, the extension portion 803 has significantly less structure than the embodiment shown in FIGS. 2A and 2B. Irrespective of whether the extension portion 803 comprises mesh 806, a stent frame 820, or any other configuration, stent 802 may be collapsible, similar to a traditional stent. Alternatively or additionally, the stent 802 may be an autoexpandable stent capable of radial expansion such that, when deployed within an artery, the stent 802 facilitates secure anchoring therein and/or the long term stability of the device 800 by way of radial force. Accordingly, in this at least one embodiment, the extension portion 803 is configured to move between a collapsed configuration having a smaller diameter for delivery and/or retrieval and an expanded (or deployed) configuration having a larger diameter and capable of anchoring the device 800 within arterial walls. As shown in FIG. 3A, for example, extension portion 803 extends from a first end 850 (where an exemplary tip connector 808 may be located, for example), to a second end 852 where the flange portion 805 is located. As shown in FIGS. 3A-3D, the stent 802 may optionally comprise an anchor portion to facilitate secure placement of the stent 802 when positioned within a body. As shown in FIGS. 3A-3C, in at least one embodiment, the optional anchor portion comprises a flange portion 805 that extends from the proximal end of the extension portion 803 of stent 802. Flange portion 805 has an inner diameter (shown as D1 in FIG. 3A) and an outer diameter (shown as D2), whereby D2 is larger than D1. The flange portion 805 may comprise any length and/or outer diameter D2 that is effective to impede the progression of the stent 802 within an artery when positioned within a body. In other words, while the inner diameter D1 may be less than or equivalent to the diameter of the proximal opening of the artery in which the extension portion 803 is positioned (the "arterial opening"), the outer diameter D2 of the flange portion 805 is greater than the diameter of the arterial opening such that the stent 802 cannot be easily dislodged from its position by the blood flowing through the arterial opening. Additionally, when a stent 802 having flange portion 805 is placed within an arterial opening, the flange portion 805 may further provide an additional support structure over the wall of the aortic arch 104 at the entrance of the supra-aortic branches 114, 116, 118. In at least one embodiment, the flange portion 805 is between about 3 mm and about 5 mm in length.

Optional flange portion 805 may be configured to move between a collapsed position having a smaller diameter for delivery and/or retrieval of the device 800 (see FIGS. 7A and 7B) and an expanded position having a larger diameter (see FIG. 3A). For example, in at least one embodiment, the flange portion 805 is comprised of an autoexpandable material such that when the flange portion 805 is released from a delivery tool, the flange portion 805 automatically moves into the expanded position to assist in anchoring the device 800. Flange portion 805, as shown in the embodiments shown in FIGS. 3A-3C, comprises mesh 806 having multiple wires. In another embodiment, and also as shown in FIG. 3C, the anchor portion comprises a planar flange 810 comprised of metal, plastic, or any other material suitable for such a flange portion 805.

Furthermore, instead of optional flange portion 805, the optional anchor portion of the stent 802 may comprise two or more wings 809 extending from the proximal end of the extension portion 803 as shown in FIG. 3D. In at least one embodiment, each of the wings 809 is defined by wire folded over into a petal-like configuration. The plane of each wing 809 may be left as an open space (as shown in FIG. 3D), or covered by mesh 806 or any other suitable material. When the embodiment of the stent 802 having two or more wings 809 is positioned within a body, the wings 809 contact the underlying tissue at intervals, thereby utilizing a minimized structure as compared to the embodiment of the stent 802 comprising the flange portion 805, which reduces the potential for damage to the underlying epithelium while still anchoring the stent 802 in the appropriate position.

Similar to the flange portion 805, the wings 809 are sized and configured to impede the progression of the stent 802 within an artery when positioned within a body. Additionally, when the stent 802 is placed within a proximal opening of the innominate artery 114 or the left subclavian artery 118, the wings 809 may further provide a support structure over the wall of the aortic arch 104 at the entrance of the supra aortic branches 114, 118. While illustrated in a petal configuration in FIG. 3D, it will be noted that the wings 309 may comprise any suitable shape or configuration and that each wing 809 of the stent 802 need not have the same length and/or configuration. In addition, in the exemplary embodiment shown in FIG. 3D, the wings 809 of the stent 802 may further comprise one or more radiopaque markers 814.

Also similar to the anchor portion comprising flange portion 805, the anchor portion comprising wings 809 are configured to move between a collapsed position having a smaller overall diameter (not shown) and an expanded position having a larger overall diameter D (see FIG. 3D). In at least one embodiment, each of the wings 809 is hingedly coupled with the extension portion 803 and biased to the expanded position. As such, when the wings 809 are not held in the collapsed position, the wings 809 automatically move to the expanded position. As described in further detail herein, movement of the stent 802 (and thus the wings 809 when attached thereto) between the collapsed and expanded positions facilitates delivery/retrieval and the long term stability of the stent 802 within an artery.

In at least one embodiment of device 800 of the disclosure of the present application, each stent 802 comprises an autoexpandable metallic stent comprising a distal cylindrical tube (extension portion 803). In an exemplary embodiment, extension portion 803 is approximately 1.0 cm to 2.5 cm in length. In at least one embodiment of device 800, the diameter of each stent 802 is approximately 6 to approximately 8 mm. Suitable material for a stent 802 includes, but is not limited to, stainless steel, cobalt-chromium-nickel-molybdenum-iron alloy, tantalum, nitinol, nickel-titanium, polymer materials, and various shape-memory polymers known in the art, including polyurethane, polytetrafluoroethylene or polytetrafluoroethene (PTFE), other synthetic materials, and/or any non-thrombogenic material.

Referring back to FIGS. 2A-2D, in addition to the two or more stents 802, the device 800 also comprises at least one deflection component 804. Deflection component 804 may be combined with a stent 802 (such combination referred to herein as a "deflection stent 807"), or be positioned independently on the device 800. For example, some exemplary embodiments of the device 800 shown in FIGS. 2A-2D, comprise one deflection stent 807, one stent 802 that does not comprise a deflection component 804, and one independent deflection component 804.

Deflection component 804 is operable to divert a clot or debris within the blood flow—an embolus, for example—from entering an artery to which the deflection component 804 is applied, while nevertheless not significantly affecting flow resistance. Where a deflection component 804 and stent 802 form a deflection stent 807, the deflection component 804 is positioned across the open proximal end of the stent 802 to prevent an embolus or debris in the blood from entering the interior of the stent 802 (see FIGS. 2B and 3A-3C). Alternatively, where the deflection component 804 is independently positioned on the device 800, the deflection component 804 comprises a frame 818 that defines an interior, with a deflection portion extending across the same (convex struts 812, for example). The frame 818 may comprise any configuration, provided the interior of the frame 818 is sufficiently sized to cover at least a portion of the ostium of an aortic branch to which the deflection component 804 is applied. For example, as shown in FIGS. 2A and 2B, the frame 818 may comprise a circular or oval configuration. Furthermore, the deflection component 804 (including, where applicable, the frame 818 and/or convex struts 812) may comprise material of the same and/or similar to the material of the other portions of the device 800, and/or may also be a combination of a metal plus polyurethane, polytetrafluoroethylene (PTFE), or other synthetic material(s).

As shown in FIGS. 2A-3A, in at least one exemplary embodiment, deflection component 804 comprises two or more convex struts 812 spanning the frame 818 and traversing the diameter of the deflection component 804. It will be appreciated that the number and size of the convex struts 812 present on the deflection component 804 may be customized according to a user's preferences and/or patient specifications. Furthermore, each convex strut 812 need not be configured identically; indeed, deflection component 804 may be configured to employ various combinations of strut 812 diameter, intervals, and heights. Moreover, the convex struts 812 may also comprise varying cross-sectional areas and/or a non-spherical profile of the convex envelope.

For example, in at least one embodiment of the deflection component 804 of the present disclosure, the diameter of each convex strut 812 is approximately 0.25 mm to approximately 1.0 mm, and the distance between each convex strut 812 is approximately 0.75 mm to approximately 1.0 mm. In at least one exemplary embodiment, the diameter of each convex strut 812 is approximately 0.75 mm and the distance between each convex strut 812 is approximately 0.75 mm, which has been found to provide beneficial deflection efficacy with respect to emboli while affecting only negligible change in flow resistance through the underlying artery.

In at least one embodiment, convex struts 812 may be semi-rigid or flexible to facilitate delivery of the device 800 and/or to allow the passage of a catheter stent device for stenting the artery to which the deflection component 804 is applied in the event such artery develops an atherosclerotid plaque, for example. In an exemplary embodiment, the strut 812 shape can be convex or semi-convex. This configuration facilitates the constant "washing" of the struts 812 by the aortic blood flow, which supports unhindered blood flow through the underlying artery and avoids local thrombosis. For example, if an embolus lands on a strut 812, the strut shape causes the embolus to wash off to the periphery, not only preventing the embolus from entering the underlying artery and thus the vascular brain system, but also deflecting the embolus away from the ostium of the artery. In this manner, the convex or semi-convex shape of the struts 812 ensures that blood flow through the deflection component 804 does not become restricted or blocked.

Furthermore, the convex struts 812 may be aligned across the deflection component 804 in any direction relative to the device 800. The orientation of the convex struts 812 relative to the device 800 determines how the struts 812 will interact with the flow field where the device 800 is applied. For example, as shown in the exemplary embodiments of device 800 of FIGS. 2A and 2B, convex struts 812 of the deflection components 804 are aligned in a direction approximately parallel to the length of the device 800. In such an alignment, when the device 800 is positioned within an aorta 100, the struts 812 are substantially parallel to the flow of blood therethrough. As such, as blood flows through aorta 100, an embolus 300 present within aorta 100 (specifically within the aortic arch 104) is guided by the blood flow along convex struts 812 and across the diameter thereof (i.e. prevented from flowing through the deflection component 804 itself). Alternatively, as shown in FIGS. 2C and 2D, the convex struts 812 may be oriented in a direction approximately perpendicular to the length of the device 800. In such a configuration, when the device 800 is positioned within an aorta 100, the blood flow will be substantially perpendicular to the strut 812 alignment and any embolus 300 present within aorta 100 will contact convex struts 812 and be deflected therefrom with little or no risk of embolus 300 being trapped therein. As referenced herein, convex struts 812 may also be positioned in a direction of (i.e., approximately parallel with), or in an oblique manner relative to, blood flow within the aortic arch 104. In application, the device 800 may be positioned within an artery to achieve any orientation of the convex struts 812 relative to the flow field that may be desired in accordance with patient specifications and/or user preference.

While the embodiments discussed herein illustrate the deflection components 804 of the device 800 as comprising convex struts 812, it will be appreciated that the deflection component 804 may comprise any configuration operable to divert an embolus or debris from entering an artery of interest. For example, in at least one embodiment, the deflection component 804 comprises a mesh (similar to, for example, mesh 806) stretched across the diameter of the deflection component 804.

Furthermore, one or more of the components of device 800 may further comprise one or more radiopaque markers 814 to aid the delivery and placement of the device 800 within a body. For example, in at least one embodiment, one or more radiopaque markers 814 are positioned on the proximal end of the device 800 to assist a user in identifying how far the device 800 should be advanced within the aortic arch 104.

Figure 4:
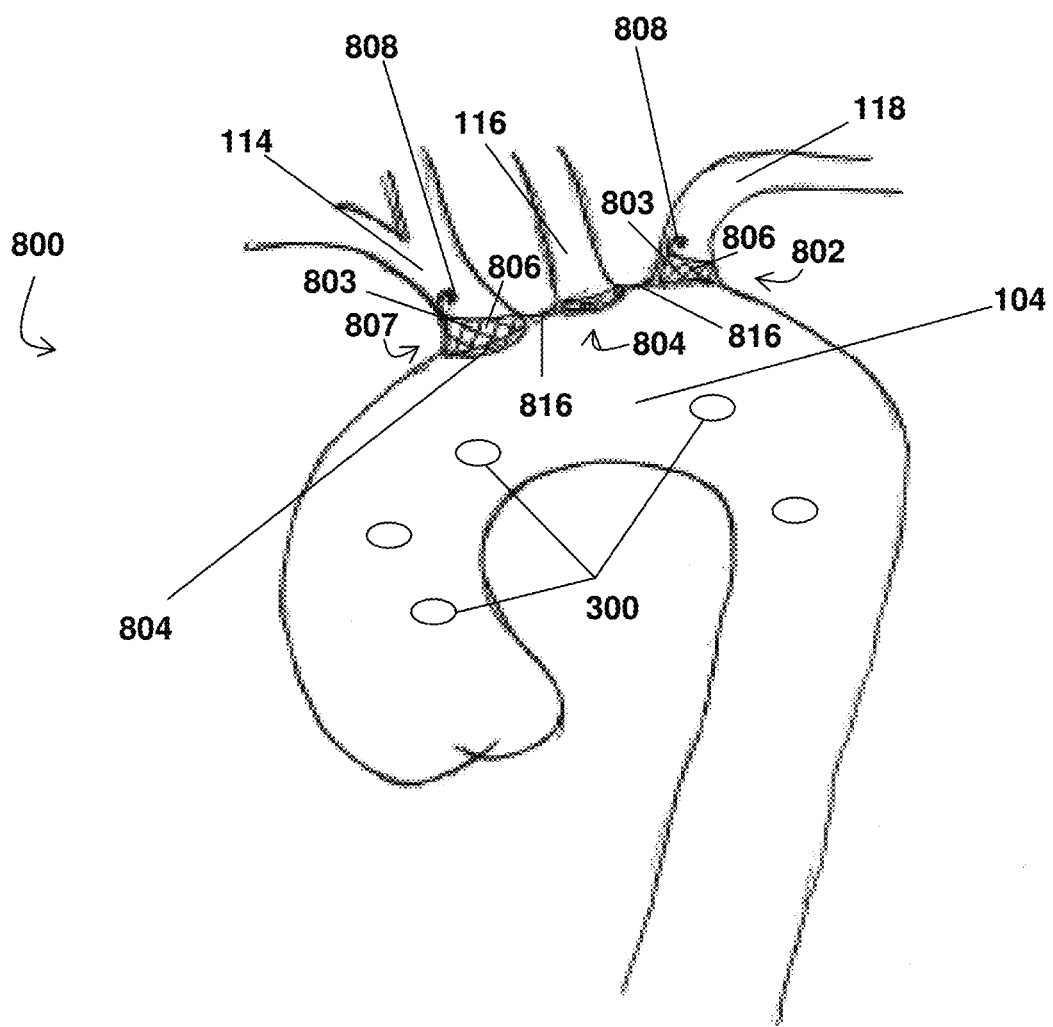
FIG. 4 shows an exemplary device for the prevention of stroke positioned within an aortic arch with stents positioned within arteries extending from the aorta and deflection components having convex struts positioned over arterial ostia, according to the present disclosure.

Now referring to FIG. 4, an exemplary device 800 for the prevention of stroke is shown positioned within a portion of an aorta 100 such that it is operable to divert emboli and/or debris from multiple aortic branches 114, 116, 118 concurrently. While the device 800 illustrated in FIG. 4 comprises stents 802 having mesh 806, connecting wire(s) 816 in a non-spring configuration, and a particular combination of a deflection stent 807, deflection component 804 and a stent 802, it will be understood that any embodiments of the device 800 of the present disclosure can be used as described herein and are capable of comparable functionality as is described in connection with FIG. 4.

As shown in FIG. 4, in at least one application, device 800 is positioned within the aortic arch 104 to deflect emboli 300 and/or debris from entering the innominate and left common carotid arteries 114, 116. In this embodiment, device 800 sits within the outer curvature of the aortic arch 104 such that it is seated against or at least partially within the entrances of the supra-aortic branches 114, 116, 118. The device 800 is anchored in position at least by a deflection stent 807 positioned within the innominate artery 114 and a stent 802 positioned within the left subclavian artery 118. Placement of the device 800 as described herein protects a patient against ischemic stroke, and also does not significantly interfere with the blood flow rates or resistance through the aortic branches or the proper perfusion of the protected arterial territories.

Deflection stent 807 is positioned so that the extension portion 803 thereof is within at least a portion of the innominate artery 114 and the deflection component 804 of the deflection stent 807 is positioned over the entrance or ostium of the innominate artery 114. Upon deployment of the stent 802 of the deflection stent 807 within the innominate artery 114, the stent 802 of the deflection stent 807 is moved to the expanded position and the distal cylindrical portion of the deflection stent 807 (the extension portion 803 of the stent 802) anchors device 800 by way of applying radial force within the artery 114.

In addition to deflection stent 807, in the exemplary embodiment shown in FIG. 4, an independent stent 802 (not comprising a deflection portion 804) is positioned and deployed within the left subclavian artery 118. Similar to the stent 802 of the deflection stent 807, the stent 802 is moved to the expanded position when deployed and the distal cylindrical portion thereof (the extension portion 803) anchors the device 800 by way of applying radial force within the artery 118. While neither the deflection stent 807 nor stent 802 shown in the embodiment of FIG. 4 have an anchor portion (flange portion 805 or wings 809), in an alternative embodiment where deflection stent 807 and/or stent 802 comprise optional flange portion 805 or wings 809, such flange portion(s) 805/wings 809 can further assist in preventing the stent 802 or 807 (as applicable) from advancing further into the artery in which it is placed by having an outer diameter D2 that exceeds the diameter of the relevant arterial opening.

In addition to the active anchoring achieved by deploying stents 802 and 807 within the respective arteries 114, 118, the configuration of the device 800 itself facilitates secure placement within the aorta 100 and prevents its components from advancing further into the supra-aortic arterial branches in compliance with the blood flow therethrough. As previously described, the components of the device 800 are linked together via the connecting wire(s) 816. This linked configuration, in conjunction with the flow fields through the aorta 100 and supra-aortic branches 114, 116, 118, acts to further anchor the device 800 in position. For example, when the device 800 is positioned within an aorta 100 as shown in FIG. 4, blood flow into the innominate artery 114 applies pressure to the deflection stent 807 positioned therein to advance through the artery 114. Concurrently, blood flowing into the left common carotid artery 116 applies similar pressure to the deflection component 804 and blood flowing into the left subclavian artery 118 applies similar pressure to stent 802. As all components of the device 800 (e.g., 807, 804, 802 as shown in FIG. 4) are attached via connecting wire(s) 816 or otherwise, the force of the blood flow pulling the components into different arteries is translated to the connecting wire(s) 816 spanning the aortic arch 104, thus securing the device 800 against the supra-aortic wall. In this manner, the linked configuration of the components not only prevents the independent components from advancing further into their respective arterial branches, but also secures the device 800 in the desired position.

Due to the location of the independent deflection component 804 on the device 800, when the device 800 is positioned as shown in FIG. 4, the deflection component 804 may be disposed at or near the entrance of the left common carotid artery 116. In at least one exemplary embodiment, the deflection component 804 completely covers the entrance of the artery 116 over which the deflection component 804 is positioned. As previously described, because the linked configuration of the device 800 and the flow fields through the aortic branches secure the device 800 against the supra-aortic wall, the independent deflection component 804 does not require an accompanying stent 802 or other securing device/mechanism to hold it in position over the left common carotid artery 116. Accordingly, the independent deflection component 804 can be securely positioned over the left common carotid artery 116 to deflect emboli 300 and debris therefrom, without any component of the device 800 entering the left common carotid artery 116 and risking damage to the endothelium therein.

Figure 5A:
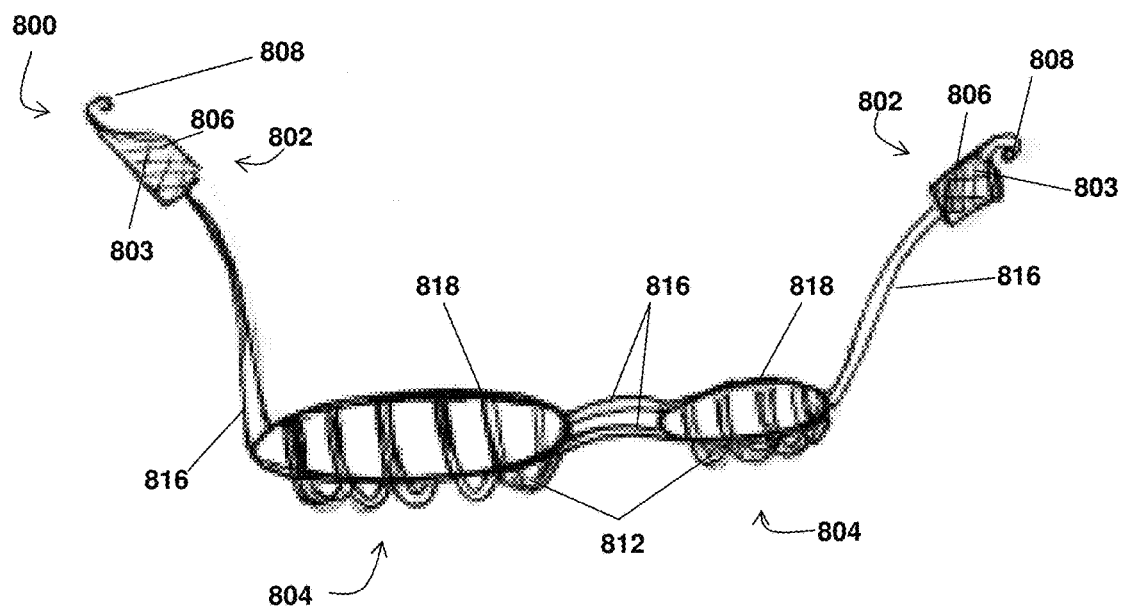
FIGS. 5A and 5B show exemplary devices for the prevention of stroke according to the present disclosure.
Figure 5B:
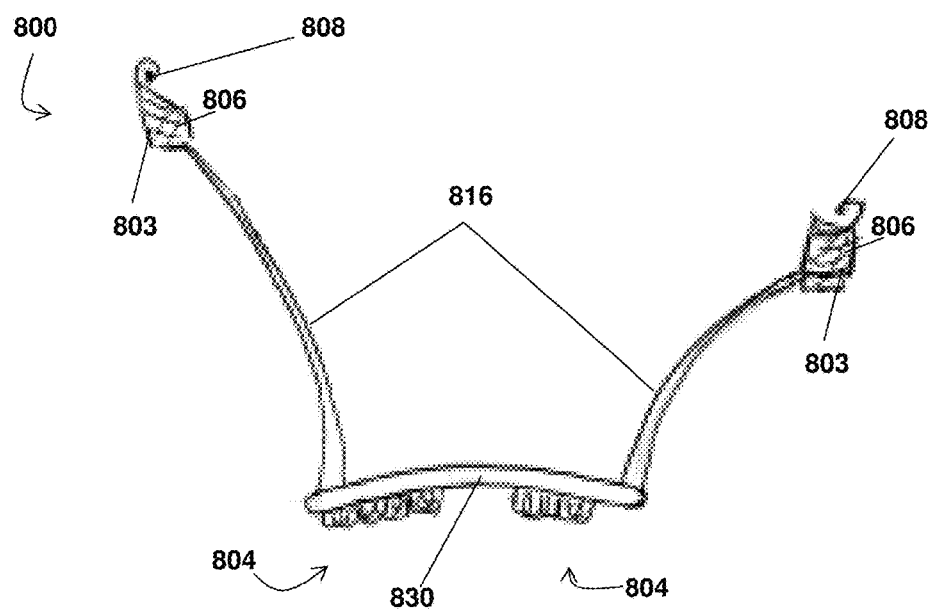

Now referring to FIGS. 5A and 5B, at least one alternative embodiment of the device 800 for preventing stroke is shown. This embodiment of the device 800 not only prevents any emboli or debris from entering the innominate or left common carotid arteries 114, 116, but also mitigates the risk of problematic thrombosis forming within the supra-aortic arterial branches at a location downstream of the deflection components 804.

In the exemplary embodiment of the disclosure, the device 800 comprises two stents 802 and two deflection components 804, each of which are positioned independently on the device 800 and linked together via connecting wires 816 or some other means. Similar to the embodiments of the device 800 described in connection with FIGS. 3A-4, the stents 802 of the embodiments shown in FIGS. 5A and 5B are for anchoring the device 800 within the desired supra-aortic arterial branches. However, unlike previously described embodiments, here the device 800 is configured such that the stents 802 can engage the arterial walls at a location that is distal to the ostium of the artery of interest.

As illustrated in FIG. 5A, a first stent 802 is coupled with a first deflection component 804 via two connecting wires 816. Such first deflection component 804 is also coupled with a second deflection component 804 by two additional connecting wires 816, and the second deflection component 804 is additionally coupled with a second stent 802 by connecting wires 816. Accordingly, all four components of the device 800 are linked together by connecting wire 816 thereby forming a single, linked unit.

While this embodiment is described as having separate connecting wires 816 to connect each of the components 802, 804 of the device 800, it will be appreciated that one or more connecting wires 816 may be integrated with all or some of the components of the device 800 to achieve the same linking effect. Alternatively, the two deflection components 804 may be integrated into a single unit 830 with connecting wires 816 connecting the first and second stents 802 to the ends thereof (see FIG. 5B). There, the single unit 830 may be comprised of any suitable material, provided such material has (or is capable of conforming to) a curvature that substantially coincides with the anatomy of the aortic arch 104 such that, in application, the deflection components 804 can be positioned over the supra-aortic openings of the desired arterial branches. Furthermore, while the device 800 shown in FIGS. 5A and 5B comprises stents 802 having mesh 806, connecting wire(s) 816 having a non-spring configuration, and a strut 812 orientation on the deflection components 804 that is perpendicular to the device 800 and thus the flow of blood when positioned within an aorta 100, it will be appreciated that any other embodiments of the device 800 (and/or its components) described herein can be employed. For example, and without limitation, one or more of the stents 802 may comprise a stent frame 820, one or more of the struts 812 of a deflection component 804 may have another alignment relative to the device 800 (i.e. substantially parallel thereto or positioned at some other angle) and/or be sized, shaped or spaced differently, a deflection component 804 may comprise an alternative deflection mechanism (e.g., a mesh or other material or configuration), and/or connecting wire(s) 816 may have a spring configuration.

Figure 6:
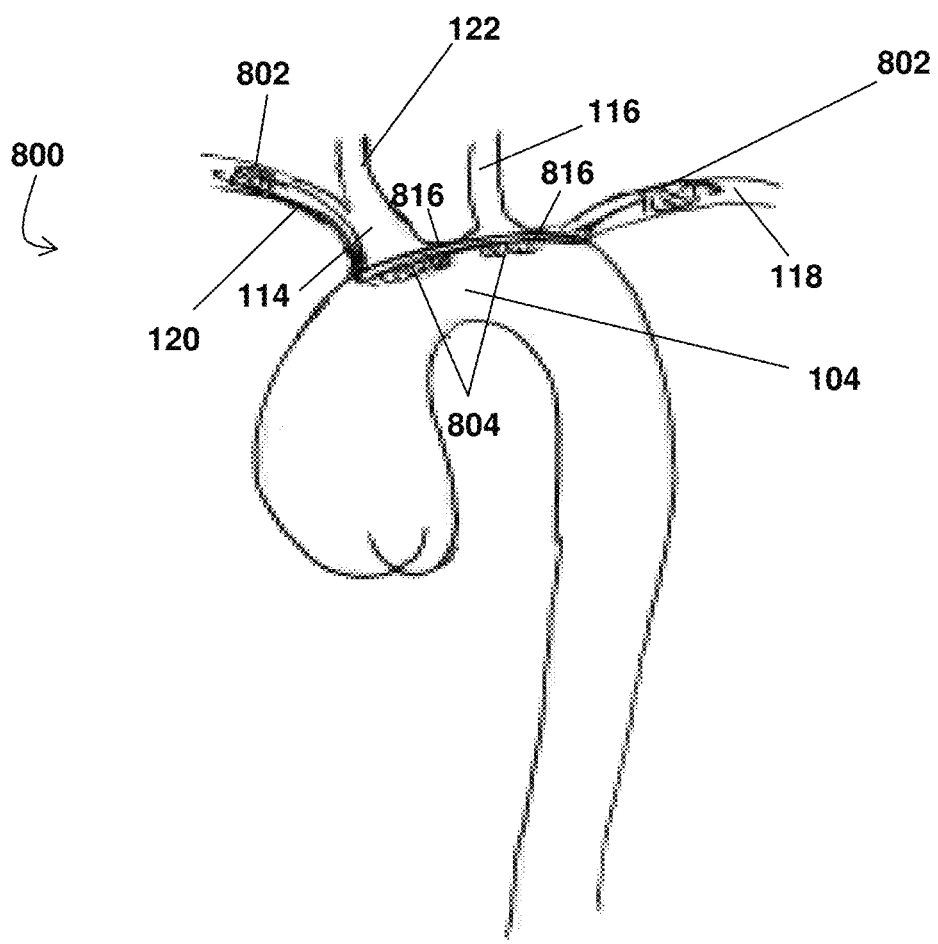
FIG. 6 shows the exemplary device of FIGS. 5A and 5B positioned on an aortic arch with stents positioned within arteries extending from the aorta and deflection components having convex struts positioned over arterial ostia according the present disclosure.

FIG. 6 shows the embodiments of the device 800 for the prevention of stroke of FIGS. 5A and 5B positioned within an aorta 100. Similar to the embodiments described in connection with FIGS. 3A-4, this embodiment of the device 800 is operable to concurrently divert emboli and/or debris from multiple aortic branches via deflection components 804. In at least one application of the device 800, device 800 is positioned within the aortic arch 104 to deflect emboli and/or debris from entering the innominate and left common carotid arteries 114, 116 and thus prevent the same from entering the cerebral vascular system. Specifically, device 800 sits within the outer curvature of the aortic arch 104 such that the deflection components 804 are seated against the ostia of the supra-aortic branches 114, 116. However, unlike previous embodiments where the stents 802 anchor directly within or adjacent to the ostial openings of the arteries, here the stents 802 are positioned higher up within the subclavian arteries 120, 118 (i.e. at locations distal to the ostia).

As previously discussed, the various supra-aortic arterial branches supply oxygenated blood flow to different parts of the body. For example, while the innominate and left common carotid arteries 114, 116 supply blood flow to the cerebral vascular system, the left subclavian artery 118 mainly supplies blood to the left brachial arteries. As such, the devices, systems and methods described herein focus on deflecting emboli and debris away from the innominate and left common carotid arteries 114, 116 that provide blood flow to the brain. However, even non-thrombogenic medical implants introduce an increased likelihood of thrombosis because the endothelium becomes more sensitive and prone to clots where a device contacts the same. Consequently, deploying a stent 802 within the ostium of the innominate artery 114 increases the risk of lesion or thrombus formation therein to some degree. The innominate artery 114 (otherwise known as the brachiocephalic trunk) divides into the right subclavian artery 120, which supplies blood flow to the right brachial arteries, and the right common carotid artery 122, which—like the left common carotid artery 116— supplies blood flow to the cerebral vascular system. Accordingly, any lesions or thrombosis formed within the brachiocephalic trunk presents a risk of ultimately blocking blood flow to the brain and/or releasing an embolus 300 into the cerebral vascular system at a point downstream from the deflection component 804.

To mitigate the risk of lesion and/or clot formation resulting in stroke, the embodiments of the device 800 of FIGS. 5A-6 are configured such that the first stent 802 may be deployed within the right subclavian artery 120, while the first deflection component 804 is positioned over the ostium of the innominate artery 114. In this manner, should any thrombogenic effect result from placement of the first stent 802, the embolus 300 will be released in the right subclavian artery 120 and flow into the peripheral arteries rather than the cerebral system. Accordingly, placement of these embodiments of the device 800 within the aortic arch 104 are more gentle on the innominate artery 114 and help to prevent lesions and/or thrombosis from forming in the brachiocephalic trunk.

As shown in FIG. 6, the second stent 802 of the device 800 and the connecting wire(s) 816 connected thereto may also be configured for placement and deployment higher up in the left subclavian artery 118. As previously noted herein, placement of a device against the endothelium may make the endothelium sensitive and more prone to clots. Because of this, placing and anchoring the second stent 802 higher up in the subclavian artery 118 (away from the ostium thereof) may be preferable to reduce the risk of blockage.

In application of at least one embodiment of the device 800, the first stent 802 is positioned so that the extension portion 803 thereof is within the right subclavian artery 120 and the first deflection component 804 is positioned over the entrance/ostium of the innominate artery 114. Upon deployment of the first stent 802 within the innominate artery 114, the first stent 802 is moved to the expanded position and the distal cylindrical portion of the extension portion 803 anchors device 800 by way of applying radial force within the artery 120. In addition to the first stent 802, in the exemplary embodiment shown in FIG. 6, a second stent 802 is positioned so that the extension portion 803 thereof is within at least a portion of the left subclavian artery 118. As shown in FIG. 6, in at least one embodiment, the second stent 802 is positioned at a location distal to the ostium of the left subclavian artery 118. After the second stent 802 is positioned as desired, the second stent 802 is moved to the expanded position for deployment. Accordingly, the extension portion 803 anchors the device 800 within the left subclavian artery 118 by way of applying radial force therein.

It will be appreciated that while FIG. 6 illustrates the second stent 802 positioned higher up in the subclavian artery 118, second stent 802 may alternatively be positioned at or near the ostium of the left subclavian artery 118 similar to the placement of independent stent 802 in FIG. 4. Furthermore, where the second stent 802 is positioned at or near the ostium of the left subclavian artery 118, the second stent 802 may optionally comprise an anchor portion (e.g., flange portion 805 or wings 809) to further assist in securing the second stent 802 (and, thus, the device 800) in position.

In the embodiment shown in FIG. 6, the device 800 is configured such that when the first and second stents 802 are properly positioned and deployed within their respective arteries 120, 118, the first deflection component 804 is positioned at or near the ostium of the innominate artery 114 and the second deflection component 804 is positioned at or near the ostium of the left common carotid artery 116. In at least one exemplary embodiment, each deflection component 804 completely covers the ostium of the artery over which such deflection component 804 is positioned. The deflection components 804 do not require additional anchoring devices/mechanisms to hold them in position over the arterial ostia of interest. Instead, the configuration of the embodiments of the device 800 shown in FIGS. 5A-6 and the flow fields through the aortic branches facilitate secure placement of the device within the aorta 100 and prevents the components 802, 804 of the device 800 from moving and/or advancing further into the supra-aortic arterial branches. Particularly, because the components 802, 804 of the device 800 are linked, the stents 802 secure the deflection components 804 in position, while the deflection components 804 and connecting wire(s) 816, single unit 830, and/or optional anchor portion (e.g., flange portion 805 or wings 809) (if any) prevent the stents 802 from advancing further into their respective arterial branches. Furthermore, when the device 800 is positioned as shown in FIG. 6, blood flow into the supra-aortic arterial branches applies pressure to the stents 802 and deflection components 804 thus further securing the deflection components 804 and portions of the connecting wire(s) 816 and/or single unit 830 against the supra-aortic wall. In this manner, the deflection components 804 (and thus the device 800) can be securely positioned over the innominate and left common carotid arteries 114, 116 to deflect emboli and debris therefrom, without risking damage to the endothelium of such arteries due to stent placement therein.

In sum, the disclosure of the present application provides a device 800 configured for delivery to the aortic arch 104 and the supra-aortic arteries stemming therefrom (namely the innominate artery 114, the left common carotid artery 116, and the left subclavian artery 118) for use in preventing stroke in patients having cardiovascular disease or exhibiting/experiencing other risk factors for ischemic stroke. Positioning the device 800 as shown in FIGS. 4 and 6 effectively prevents a patient from having a stroke by providing cerebral protection by way of deflecting any emboli 300 present in the blood stream away from the vessels that feed the brain and instead routing such emboli 300 to a location where they may be easily and safely removed. Specifically, an embolus 300 is prevented from entering the innominate artery 114 and the left common carotid artery 116 by the deflection components 804, but allowed to enter the left subclavian artery 118 (as the stent 802 positioned therein does not have a deflection component 804 affixed thereto). Because the innominate and left common carotid arteries 114, 116 supply blood flow to the brain, in this example, device 800 thus prohibits the embolus 300 from advancing to the vascular brain system, which significantly reduces a patient's risk of ischemic stroke. Instead, the embolus 300 is allowed to flow into the peripheral arterial system—such as the femoral or iliac arteries, for example—where the now peripheral arterial embolus 300 can be filtered or sucked from the blood stream using an appropriate medical or surgical procedure (for example, fibrinolitic drugs, surgical embolectomy, endovascular embolus suction, etc.) that, unlike stroke, can be provided with little residual effect. Accordingly, by "deflecting" the emboli 300 from the vascular brain system and "rerouting" it to the arterial system, use of the device 800 avoids disabling stroke, decreases mortality, and avoids physical impairment and the associated poor quality of life.

Application of the device 800 may be particularly useful to patients who have undergone medical procedures associated with a high risk of stroke and/or blood clots being released following the same (e.g., transcatheter aortic valve implantation ("TAVI"), mitral valve replacement, calcific mitral valve insufficiency, balloon dilation, etc.). For example, the general risk of stroke after TAVI is about three percent (3%), which increases to about six to ten percent (6-10%) thirty days following the procedure, and again to about seventeen to twenty-four percent (17-24%) one year following the procedure. As such, while TAVI (or similar procedures) is often used to repair a patient's heart and/or circulatory system, the procedure often results in brain damage due to its side-effect of increasing the occurrence of blood clots.

The devices, systems and methods of the present disclosure can be used in connection with such patients to divert the resulting clots. Moreover, the devices, systems and methods described herein are also particularly applicable to patients who cannot receive anticoagulants, are prone to clots forming in the left atrial appendage and entering the bloodstream, or simply present an elevated risk for brain damage due to stroke. The risk of brain damage can also generally be reduced with the elderly by employing the devices, systems and methods disclosed herein.

Exemplary embodiments of a system 900 for preventing stroke of the present disclosure will now be described in connection with FIGS. 7A-10B. System 900 comprises a device 800 and at least one delivery device. The specific configuration and measurements of the delivery device may be modified, depending on the design of the device 800 to be delivered and/or particular aspects of such device's 800 components.

Figure 7A:
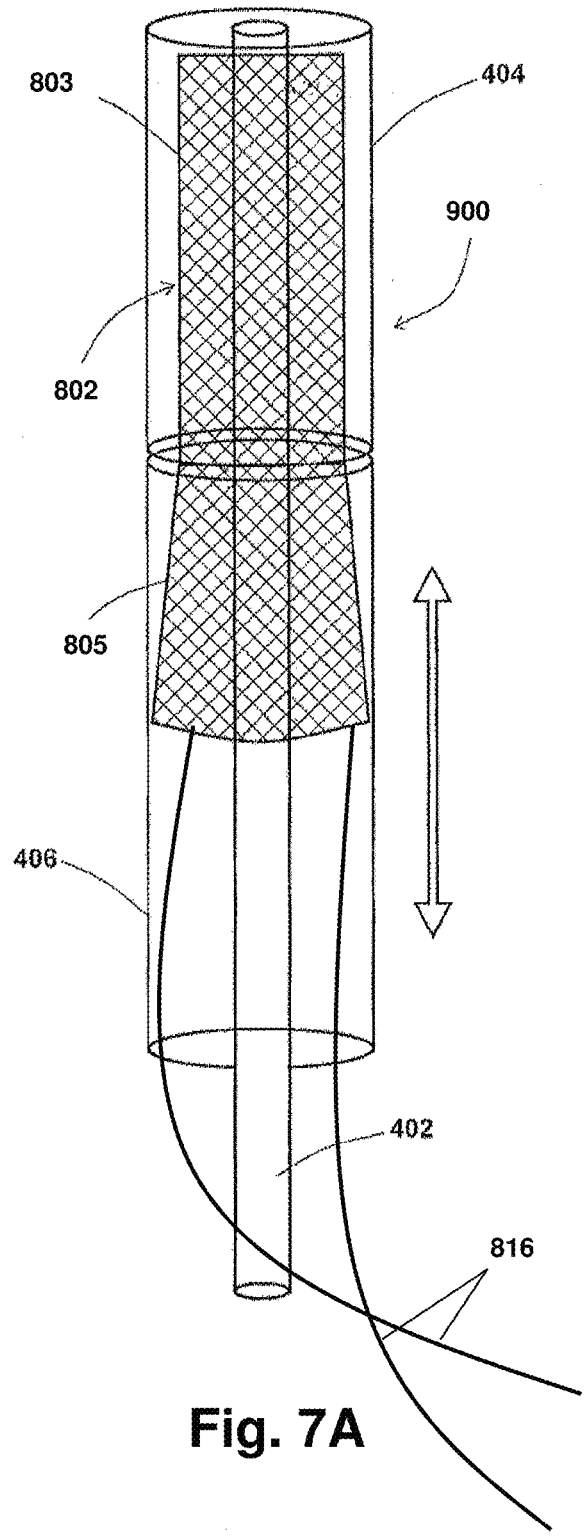
FIG. 7A shows an exemplary embodiment of a system for preventing stroke, according to the present disclosure.
Figure 7B:
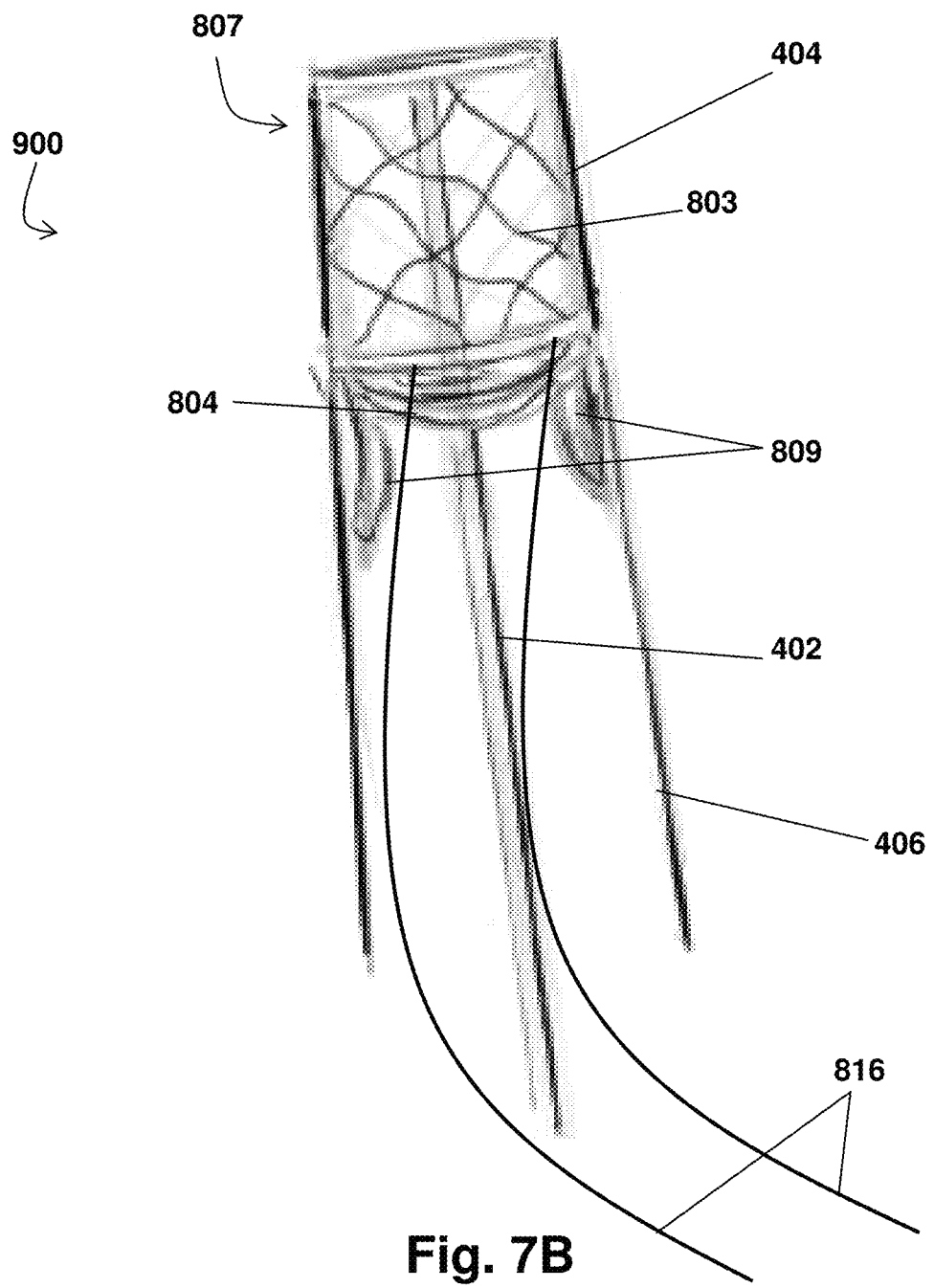
FIG. 7B shows an exemplary embodiment of a system for preventing stroke, the system comprising a device having two or more wings, according to the present disclosure.

As shown in FIGS. 7A and 7B, and especially where one or more of the stents 802/807 of the device 800 comprises an anchor portion (flange 805 or wings 809, for example), certain embodiments of the delivery device of system 900 comprise at least one hypotube 402. The hypotube 402 has a distal end and a proximal end, and in at least one exemplary embodiment, hypotube 402 comprises a folder 404 coupled to the distal end of hypotube 402. The hypotube 402 is configured to facilitate delivery and deployment of the device 800 within a body.

In the embodiments shown in FIGS. 7A and 7B, the device 800 of the system 900 comprises a stent 802 (shown in FIG. 7A), a deflection component 804 (independent component not shown), and a deflection stent 807 (shown in FIG. 7B), all coupled via connecting wire(s) 816. In this embodiment of system 900, the delivery device of the system 900 comprises at least two hypotubes 402—one for the stent 802 and one for the deflection stent 807—as these stents 802, 807 comprise flange portion 805 and wings 809, respectively. Stent 802 of device 800 is shown in FIG. 7A positioned within at least part of folder 404 and with connecting wire(s) 816 extending from the stent 802 through a sleeve 406. As seen in this embodiment of stent 802, the stent 802 comprises optional flange portion 805 that is also positioned within at least part of a sleeve 406 and around hypotube 402 proximal to folder 404. Sleeve 406, as shown in this exemplary embodiment, slidingly engages hypotube 402 and may be moved in a forward or backward direction as indicated by the arrow in the Figure.

FIG. 7B illustrates an embodiment of a second hypotube 402 of system 900 housing deflection stent 807. In this at least one embodiment, the deflection stent 807 is shown comprising wings 809, which are in the collapsed position within at least part of a sleeve 406 and around hypotube 402 proximal to folder 404. Stent 802 and/or deflection stent 807 may be compressed by a sleeve 406 and folder 404 such that both the extension portion 803 and optional anchor portion (e.g., flange portion 805 and/or the wings 809 (as applicable)) are in their collapsed positions. In at least one embodiment, at least part of system 900 has a diameter of about 7 Fr to about 8 Fr (2.3 to 2.7 mm), with an exemplary device 800 having a compressed diameter of about 1.8 to about 2.0 mm.

While both FIGS. 7A and 7B illustrate embodiments of the device 800 of the system 900 comprising either optional flange portion 805, planar flange 810, or wings 809, any stent 802 and/or deflection stent 807 configuration described in the present disclosure may be employed. Furthermore, the folder 404 is an optional component of the hypotube 402 and may not be necessary where a stent 802/807 housed within the hypotube 402 does not comprise an anchor portion. In such embodiments, the stent 802/807 may be solely housed within (and compressed by) the sleeve 406 of the hypotube 402 with the connecting wire(s) 816 extending through either the proximal or distal end of the sleeve 406, depending on where the stent 802/807 is positioned on the device 800.

Figure 8A:
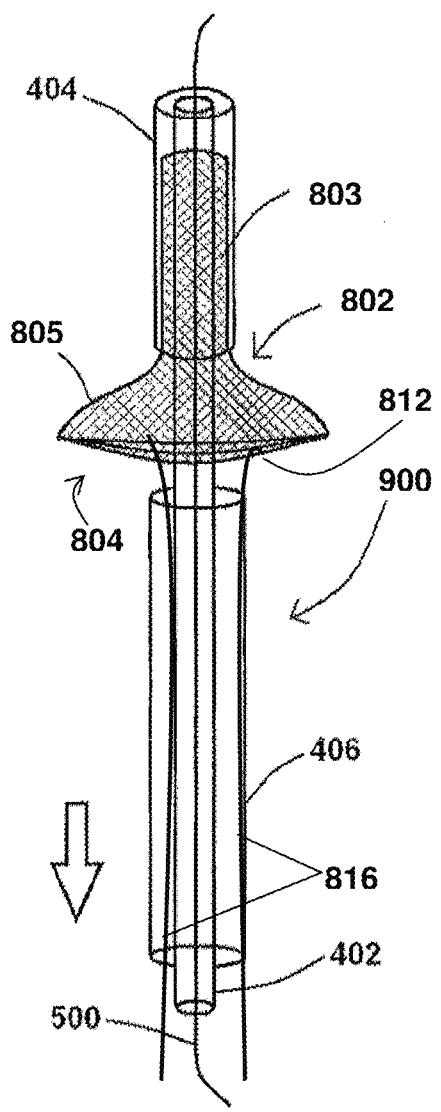
FIGS. 8A and 8B show an exemplary system of the present disclosure with portions thereof being moved to allow for device deployment, according to the present disclosure.
Figure 8B:
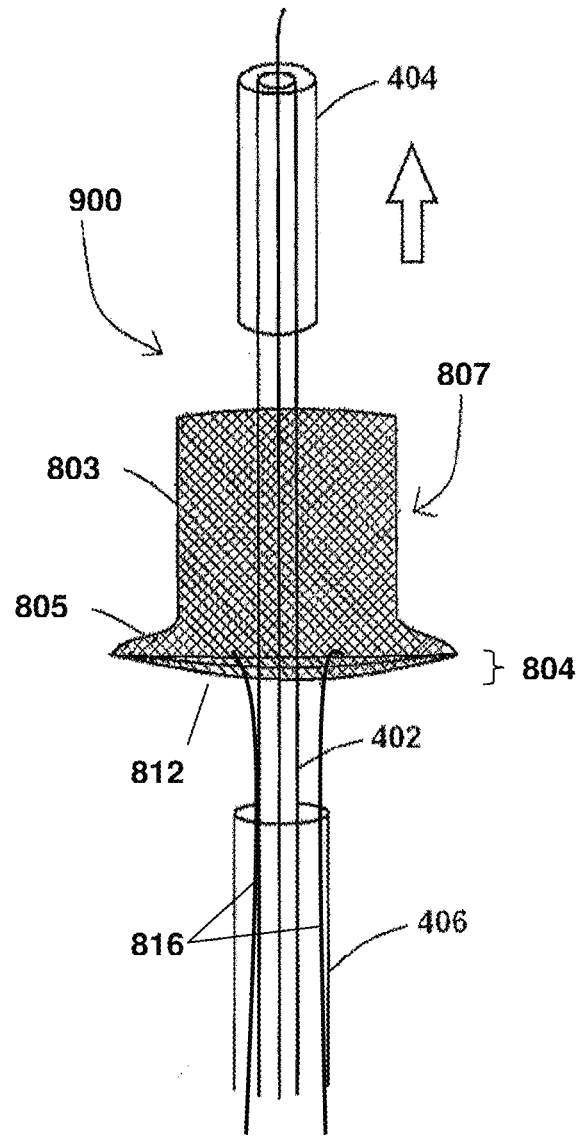

FIGS. 8A and 8B show additional exemplary embodiments of at least portions of systems for preventing stroke of the present disclosure. Specifically, FIGS. 8A and 8B illustrate an embodiment of the system 900 where the deflection stent 807 has a flange portion 805. It will be appreciated that the description of FIGS. 8A and 8B with respect to delivery of the device 800 is not limited to a device 800 comprising one or more stents 802/807 having a flange portion 805, but is equally applicable to any embodiment of the device 800 disclosed herein comprising an anchor portion such as wings 809 or a planar flange 810, for example, as delivery of the anchor portion of stent 802/807 is assisted by the bidirectional deployment permitted by a hypotube 402 comprising both a folder 404 and a sleeve 406.

As shown in FIG. 8A, the delivery device of an exemplary system 900 comprises at least one hypotube 402 to which folder 404 is coupled. In this embodiment, the delivery device further comprises sleeve 406 slidingly engaged around hypotube 402. A stent 802 (not shown) or deflection stent 807 (as shown in FIGS. 8A and 8B) may be positioned at least partially within folder 404 and sleeve 406 prior to deployment, whereby the extension portion 803 of the stent 802 may be positioned within at least part of folder 404 in a collapsed position, and whereby any proximal portion (i.e. the anchor portion—planar flange 810, flange portion 805, or wings 809, as applicable) of stent 807 may be positioned within at least part of a sleeve 406 in a collapsed position (as shown in FIGS. 7A and 7B).

As shown in FIG. 8A, device 800 may be partially deployed as follows. First, and in an exemplary method of positioning a device 800 within a body, a wire 500 (a guidewire, for example) may be advanced within a body to at or near a desired deployment location for the distal-most stent 802/807 of the device 800. When wire 500 has been advanced, hypotube 402, along with any portions of system 900 coupled to hypotube 402, may be advanced along wire 500 and positioned within the body.

As shown in FIGS. 8A and 8B, initial advancement of at least a portion of system 900 may comprise advancement of hypotube 402, folder 404, sleeve 406, and deflection stent 807 positioned within folder 404 and sleeve 406. Furthermore, because the remaining components of the device 800 are coupled with the distal-most stent 802/807 of the device 800, this initial advancement may also include advancement of any additional deflection portion(s) 804, connecting wire(s) 816, and stents 802/807 of the device 800. It will be appreciated that any additional stent 802/807 of the device 800 may also be positioned within the sleeve 406 of the hypotube 402 to facilitate the advancement and deployment thereof in conjunction with the advancement/deployment of the distal-most stent 802/807 of the device 800. Alternatively, where any additional stent 802/807 of the device 800 comprises a flange portion 805 or wings 809, such stent 802/807 may be positioned within an additional hypotube 402 to facilitate its independent advancement/deployment within the body.

When the distal-most stent 802/807 of the device 800 has been positioned within a body at or near a desired position, sleeve 406 is withdrawn toward the proximal end of hypotube 402 (in the direction of the arrow shown in FIG. 8A). However, note that this step may be performed prior to, during, or after the step of positioning the distal end of hypotube 402 at the desired location within a vessel (for example, a vessel branching off the aortic arch 104). As sleeve 406 is slid toward the proximal end of hypotube 402, the anchor portion (here, flange portion 805) of the stent 802/807 is allowed to expand as shown in FIG. 8A. Likewise, in the at least one embodiment where the stent 802/807 comprises an anchor portion comprising two or more wings 809, sliding the sleeve 406 toward the proximal end of the hypotube 402 results in the wings 809 moving to the expanded position shown in FIG. 3D. While at this step the anchor portion (i.e. flange portion 805/wings 809) is deployed, the extension portion 803 of the stent 802/807 remains within the folder 404. Accordingly, the extension portion 803 remains undeployed and does not yet engage or anchor to an arterial wall.

Further deployment of deflection stent 807 within a body is shown in FIG. 8B. Upon movement of folder 404 away from deflection stent 807 (in a direction shown by the arrow in the referenced Figure, for example), extension portion 803 of the deflection stent 807 deploys as shown in FIG. 8B. As folder 404 is moved away from stent 807 (by, for example, advancement of hypotube 402 within a body), extension portion 803 of deflection stent 807 is no longer positioned within folder 404, thereby permitting expansion/deployment of extension portion 202.

It will be appreciated that the previously described procedure can be repeated for any remaining stent(s) 802/807 of the device 800 that have an anchor portion by using additional hypotubes 402. For example, a stent 802/807 having a flange portion 805 that is positioned closer to the proximal end of the device 800 may be positioned within a separate hypotube 402 such that a user can easily position and deploy the stent 802/807 within the artery of interest. This positioning and deployment of the remaining stent(s) 802/807 may be performed prior to, during, or after the step of positioning the distal end of the first hypotube 402 holding the distal-most stent 802/807 of the device 800 within a vessel (for example, the step of deploying a deflection stent 807 within an innominate artery 114 or a stent 802 within a right subclavian artery 120). However, if the remaining stent(s) 802/807 of the device 800 do not comprise an anchor portion, only one hypotube 402 need be employed. There, the remainder of the device 800 may be positioned in a collapsed configuration within the sleeve 406 of the hypotube 402 used to deploy the proximal stent 802/807 having the flange portion 805 or wings 809, for delivery/deployment in a manner similar to the description of the delivery catheter embodiments of the system 900 set forth below. For example, in at least one embodiment, the sleeve 406 positions and delivers the remaining components of the device 800 in series (from the distal end of the device 800 to the proximal end) by positioning each component where desired and withdrawing the sleeve 406 proximally to deliver the same.

In those embodiments of the system 900 where the delivery device comprises a hypotube 402 comprising a sleeve 406, some means is necessary to facilitate retrieval of the folder 404 after it is moved distally of the stent 802/807 in connection with positioning and deploying the same. FIGS. 9A and 9B show exemplary embodiments of at least a portion of such a system 900 for preventing stroke. In at least one embodiment, the delivery device of system 900 further comprises a conical dilator 600 slidingly engaged around a hypotube 402 coupled to a folder 404. As shown in FIG. 9A, an exemplary conical dilator 600 may comprise a tapered distal end 602, wherein the tapered distal end 602 is sized and shaped to engage the inside of folder 404. To engage folder 404, conical dilator 600 may slide along hypotube 402 in a direction indicated by the arrow in FIG. 9A. An exemplary embodiment of the engagement of conical dilator 600 and folder 404 is shown in FIG. 9B.

Engagement of conical dilator 600 with folder 404, as shown in FIGS. 9A and 9B, may facilitate the removal of at least a portion of system 900 from a body after positioning a stent 802/807 of a device 800. For example, and as shown in FIGS. 8A and 8B, after deployment of a deflection stent 807 comprising a flange portion 805 within a body, the portion of system 900 comprising folder 404 is positioned, for example, further (or distally) within a vessel than deflection stent 807. Removal of the portion of the system 900 comprising hypotube 402 and folder 404 would require, for example, pulling that portion of system 900 back through deflection stent 802. As shown in the exemplary embodiments of FIGS. 8A-9B, folder 404 may, for example, become caught on deflection stent 807 and/or a portion of a body, preventing the effective and noninvasive removal of that portion of system 900.

In at least one embodiment, and by engaging folder 404 with conical dilator 600, folder 404 (along with the portion of system 900 coupled to folder 404) may be removed from a body after placement of a deflection stent 807 of device 800 as shown in FIGS. 10A and 10B. As shown in FIG. 10A, and after a deflection stent 807 has been deployed, a user of system 900 may slide a conical dilator 600 along hypotube 402 in a direction indicated by the arrow. Conical dilator 600, in the example shown in FIGS. 10A and 10B, would be sized and shaped as to fit within the spaces between convex struts 812 of deflection stent 807. After conical dilator 600 has engaged folder 404, as shown in FIG. 10B, hypotube 402 may be withdrawn from the body in a direction indicated by the arrow, and because of the engagement, folder 404 may be removed from the body without becoming caught on deployed deflection stent 807.

Now referring to an alternative embodiment of a system 900 for preventing stroke, it will be appreciated that where a device 800 of the system 900 does not comprise a stent 802/807 having an anchor portion, delivery and deployment of the device 800 may be simplified. As such, alternative exemplary embodiments of a system 900 for preventing stroke of the present disclosure comprise a delivery device comprising a delivery catheter (not shown), rather than a hypotube 402 and conical dilator 600. Such delivery catheter may comprise any delivery catheter suitable for facilitating delivery and deployment of the device 800 within a body. In at least one embodiment, the delivery catheter comprises an elongated catheter having a proximal end, an open distal end, and a lumen extending therebetween, where the lumen of the delivery catheter is configured to slidably receive the device 800 when such device 800 is in a collapsed configuration. Furthermore, as delivery and deployment of the device 800 with the delivery catheter may be achieved in conjunction with the use of a wire 500, the delivery catheter may further be configured to be mounted over and advanced through the body along a wire 500.

In application, the delivery catheter of the system 900 may be used to deliver and deploy the device 800 within a body. After the distal end of the delivery catheter is positioned within a body at or near a targeted location, the delivery catheter may be withdrawn over the device 800 slidably positioned therein. In at least one embodiment, a user/operator may pull the delivery catheter toward its proximal end, thereby sliding it over the device 800. In this manner, the delivery catheter can be removed from the body, while the device 800 remains at or near the targeted location(s). Furthermore, in at least one embodiment where the stents 802/807 of the device 800 are autoexpandable stents, withdrawing the delivery catheter from the device 800 can deploy the device 800 within a body. Specifically, in this at least one embodiment, when the delivery catheter is withdrawn and each stent 802/807 emerges from the open distal end thereof, the stent 802/807 automatically expands to its expanded configuration, thereby exerting radial force against the adjacent arterial walls and anchoring thereto.

In at least one embodiment of a system for preventing stroke of the present disclosure, system 900 comprises a device 800 comprising a deflection stent 807, a deflection component 804, and a stent 802 (all connected via connecting wire(s) 816), and a delivery device comprising a delivery catheter. The stents 802/807 of the device 800, in at least one embodiment, may be autoexpandable, i.e. stents 802, 807 having "memory" allowing each to expand to a native configuration after being retracted/compressed to fit within, for example, the delivery catheter. System 900, in at least one embodiment, may further comprise, or be used in connection with, a femoral catheterization kit known and used in the marketplace.

In at least one exemplary method of positioning device 800 within a body of the present disclosure, the percutaneous placement of the percutaneous carotid emboli rerouting device (device 800) may be performed in an angiography procedure room. Prior to positioning the components of the device 800, a user may perform a contrast aortogram, for example, to map out the aortic arch 104 and where the cerebral vessels merge with aortic arch 104. For safety, patient preparation and sterile precautions are recommended as for any angioplasty procedure.

In at least one embodiment of a method for preventing stroke, the method comprises the step of performing a percutaneous angiogram using technique(s) known in the art under local anesthesia. As referenced above, the percutaneous angiogram would map the aortic arch 104 so that a user of a device 800 and/or system 900 of the disclosure of the present application would, for example, be able to select an appropriately-sized device 800 and/or system 900 (or portion(s) thereof) when performing the procedure. A user may also introduce a wire 500 (such as guide wire as shown in FIG. 8A) to reach the innominate artery 114 and/or the subclavian arteries 120, 118. After wire 500 has been positioned, portions of system 900 may be mounted over the guide wire 500 and progressed to the level of the entrance of the innominate artery 114 and/or the subclavian arteries 120, 118 (as applicable). Said portions of system 900 may include the delivery device, and embodiments of an exemplary device 800 comprising either two stents 802 and two deflection components 804 coupled by connecting wire(s) 816 and/or a single unit 830, or a deflection stent 807, a deflection component 804 and a stent 802 coupled by connecting wire(s) 816. In system 900, the device 800 may be positioned at least partially within the delivery device to facilitate delivery and deployment of such device 800 within a body.

Deployment of device 800, in an exemplary embodiment of a method of the present application for performing the same, is as a follows. Primarily, in at least one embodiment, deployment of the device 800 may be facilitated through the use of radiopaque markers 814. Where the device 800 comprises radiopaque markers 814 on one or more of its components, prior to anchoring one or more stents 802/807 of the device 800, such markers 814 can be used to assist with ensuring proper positioning and alignment. Specifically, the user/operator can visualize the radiopaque markers 814 through fluoroscopy or other technology and position the device 800 as desired within the aortic arch 104. In this manner, the radiopaque markers 814 can facilitate placement and orientation of the device 800.

Under fluoroscopy, delivery and deployment of the device 800 may be achieved after first advancing a wire 500 within a body to at or near the desired deployment location for the distal-most stent 802/807 of the device 800. For example, where the targeted deployment location of the distal-most stent 802/807 is within or at the ostium of the left subclavian artery 118 (see FIG. 6), the wire 500 can be introduced from the right radial or brachial artery, advanced through the right subclavian artery 120, through the aortic arch 104 and thereafter into the left subclavian artery 118. When the wire 500 has been positioned as desired (e.g., either at or near the ostium of a desired artery pursuant to the embodiment of FIG. 4 or at a location higher up within the artery as shown in FIG. 6), the delivery device (that is, hypotube(s) 402 and related folders 404 or, alternatively, the delivery catheter), along with the device 800 positioned therein in a collapsed configuration (see FIG. 12B), is mounted over and advanced along the wire 500 to the targeted position.

Figure 11A:
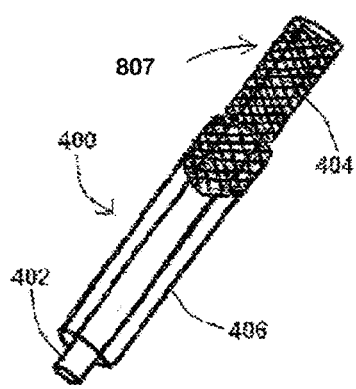
FIGS. 11A-11E show various steps of a method for positioning a stent of a device within a body, according to the present disclosure.
Figure 11B:
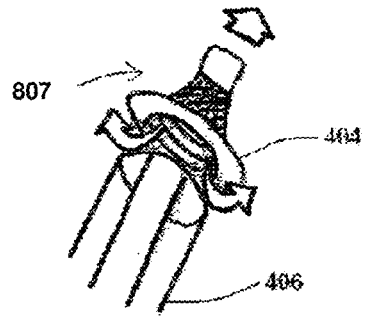
Figure 11C:
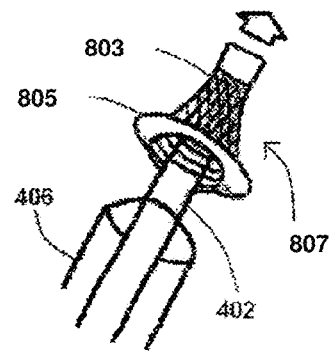
Figure 11D:
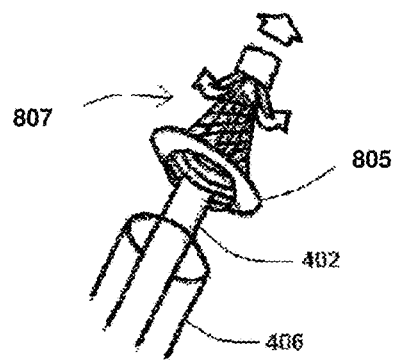
Figure 11E:
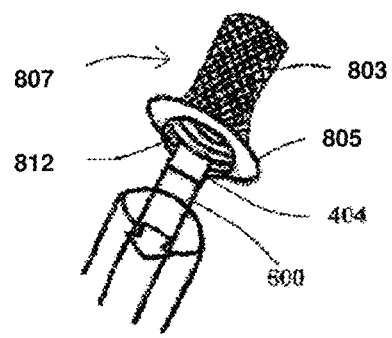

When the distal-most stent 802/807 of the device 800 is positioned within the body at or near the targeted position (e.g., within the left subclavian artery 118), the delivery catheter is pulled back from the distal-most stent 802/807 of the device 800 in the direction of the arrow shown in FIG. 11E, thereby deploying the stent 802/807 within the appropriate artery. While a user may optionally further withdraw the delivery device such that a portion of the connecting wire(s) 816 attached to the deployed stent 802/807 is also exposed within the body, at this step, the other components of the device 800 remain undeployed within the delivery catheter and do not yet engage the aortic arch 104 and/or anchor to an arterial wall.

After the distal-most stent 802/807 is deployed and securely anchored to the targeted site, this withdrawal process is repeated to deliver and deploy the remaining components of the device 800 where desired. Specifically, after the distal-most stent 802/807 is deployed and securely anchored at the targeted site, the distal end of the delivery catheter is maneuvered to deliver the remaining components of the device 800 at their targeted positions in series, starting with the next distal-most component of the device 800 that is not yet deployed. Referring back to the FIG. 6 example, after the distal-most stent 802 is deployed, the next distal-most component—the deflection component 804 connected to the stent 802 via connecting wire(s) 816—is positioned and delivered at the level of the ostium of the left carotid artery 116, followed by the next deflection component 804 being positioned and delivered at the level of the innominate artery 114, and finally the proximal-most stent 802 of the device 800 is delivered and deployed within the right subclavian artery 120. After each component of the device 800 is appropriately delivered and/or deployed and the device 800 is securely anchored within the aortic arch 104 as desired, the delivery device and wire 500 may then be removed from the body by withdrawing the same distally through the femoral or brachial artery through which at least part of the system 900 was initially introduced. Accordingly, only the device 800 of the system 900 remains deployed within the body, while the delivery device and wire 500 are removed.

Alternatively, where the device 800 comprises one or more stents 802/807 having an anchor portion (e.g., flange portion 805 or wings 809), as previously described, the delivery device of the system 900 comprises at least one hypotube 402 further comprising a sleeve 406 and conical dilator 600 associated with each such stent 802/807. In these embodiments, the method of positioning and deploying the device 800 comprises additional steps. Specifically, after the hypotube 402 (containing the device 800 therein) is advanced to the targeted location over the wire 500, sleeve 406 of such hypotube 402 is pulled back under fluoroscopy to allow for the delivery of the flange portion 805 or wings 809 of the stent 802/807 as shown in FIG. 11B. As previously described herein, the diameter of the anchor portion exceeds the diameter of the ostium of the artery in which the stent 802/807 of the device 800 is positioned and thus impedes the progression of the stent 802/807 therethrough. This provides a user/operator time to deliver and anchor the extension portion 803 of the stent 802/807 by, for example, advancing hypotube 402 as shown in FIGS. 8B and 11C. In addition, when the optional anchor portion is expanded upon delivery to the artery of interest, such structure also provides support over the aortic wall of the aortic arch 104 at the level of proximal aortic ostium in which the stent 802/807 is deployed.

When device 800 has been positioned, in this embodiment the hypotube 402 and the associated folder 404 are removed from the body, for example, by introducing the conical dilator 600 to retrieve the hypotube 402 and its components as previously described herein. In at least one example, the tapered distal end 602 of conical dilator 600 is advanced until it engages folder 404 of a hypotube 402, as shown in FIGS. 9A-10B, 11D and 11E, effectively forming a single unit (conical dilator 600+hypotube 402+optionally wire 500 (not shown)). This "unit" may then removed through the convex struts 812 as shown in FIG. 11E of a deflection stent 807, or simply by withdrawing the hypotube 402 through the stent 802 (in the case of an independent stent 802 not having a deflection component 804 attached thereto), as applicable, by pulling the hypotube 402 in the direction of the arrow shown in FIG. 11E. The unit may them be removed from the body by withdrawing the same distally through the femoral or brachial artery through which at least part of the system 900 was initially introduced.

Figure 12A:
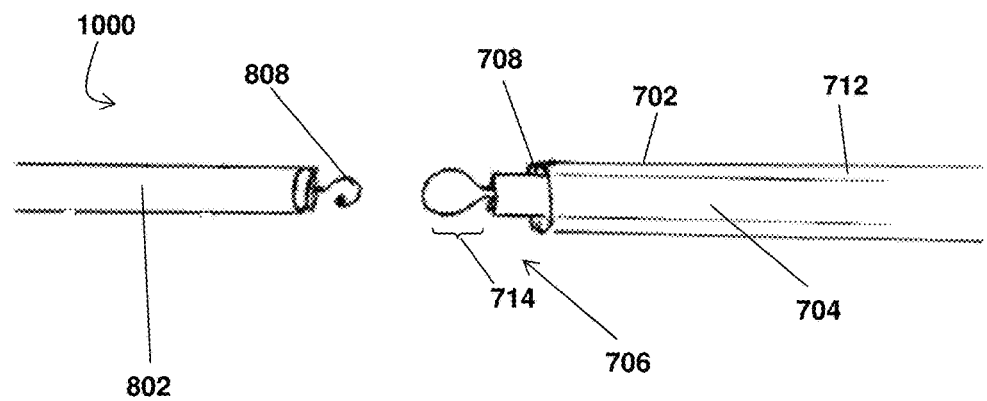
FIG. 12A shows an exemplary embodiment of a system for retrieving a device previously positioned within a body and, specifically, an embodiment of an attachment portion.
Figure 12B:
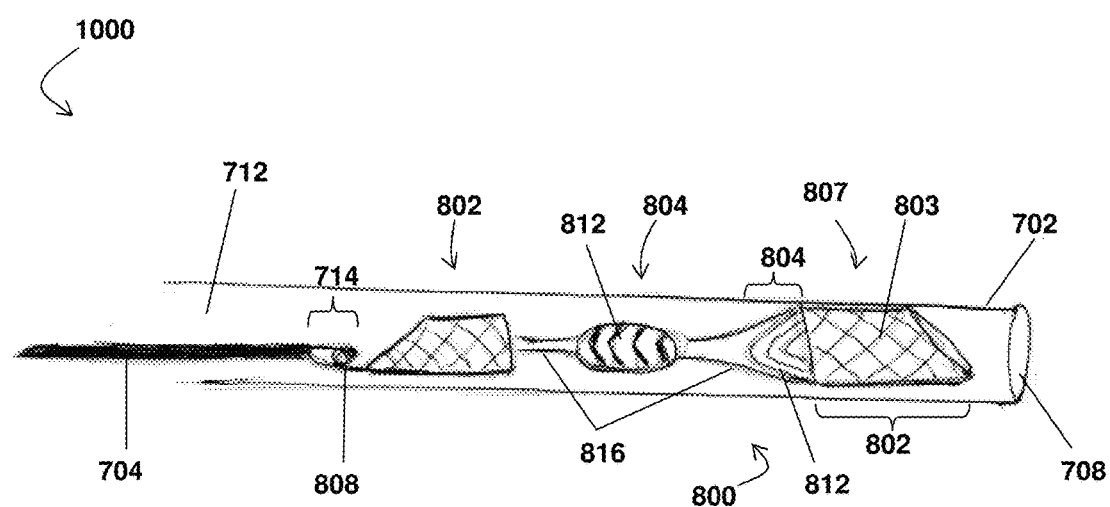
FIG. 12B shows a side view of a retrieval system according to the present disclosure.
Figure 12C:
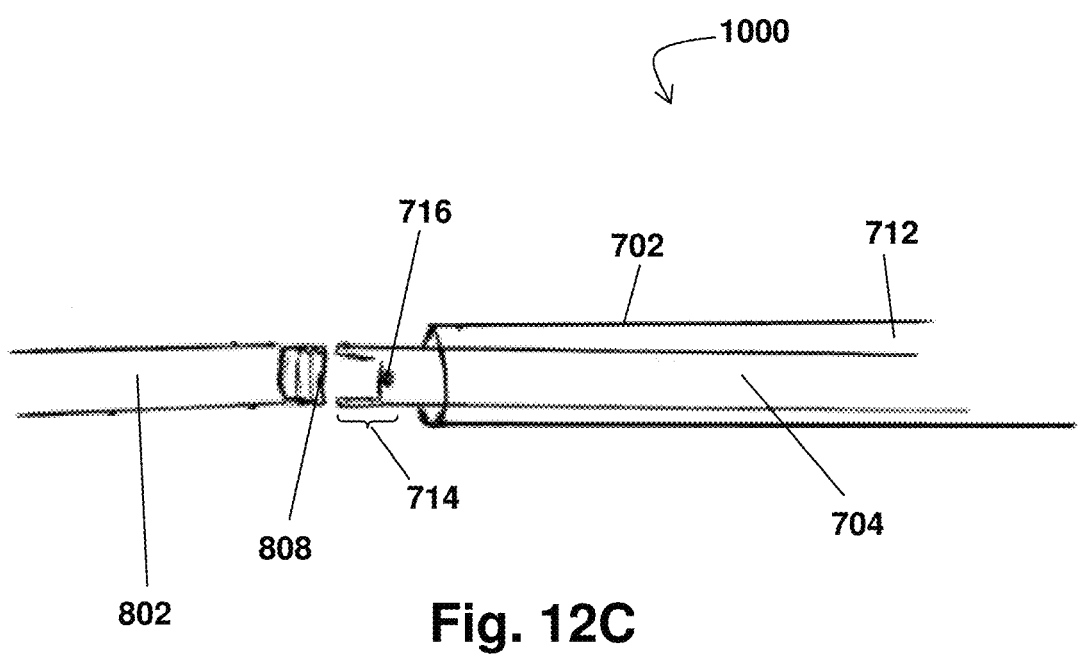
FIG. 12C shows an alternative embodiment of an attachment portions of the exemplary system for retrieving a device previously positioned within a body.

Now referring to FIGS. 12A-12C, an exemplary system 1000 for preventing stroke of the present disclosure is shown. At times, temporary placement of the devices 800 disclosed herein may be desired (as opposed to chronic or permanent placement). In such cases, it is necessary to retrieve the device 800 from the patient after a prescribed period of time has elapsed or other indications are observed. System 1000 comprises a retrieval system for use in retrieving one or more devices 800 previously positioned within the aortic arch 104.

System 1000 comprises a sleeve catheter 702, a retrieval device 704, and a device 800. The sleeve catheter 702 is configured for intravascular insertion and advancement, and comprises an open distal end 708, a proximal end 710 (not shown), and a lumen 712 extending therebetween. The retrieval device 704 is slidably disposed within the lumen 712 of the sleeve catheter 702 and comprises a proximal end (not shown) for manipulation by a user/operator and a distal end 706 configured for advancement through the open distal end 708 of the sleeve catheter 702. The distal end 706 of the retrieval device 704 further comprises one or more attachment portions 714 positioned thereon, each of which are configured to engage one or more components of the device 800.

The retrieval device 704 may comprise any configuration suitable for slidably advancing through the lumen 712 and through the open distal end 708 of the sleeve catheter 702. It will be appreciated that the specific configuration of the retrieval device 704 and its one or more attachment portions 714 can be selected and/or adapted to correspond with the configuration of the device 800 and/or components thereof to be retrieved. For example, in the embodiments shown in FIGS. 12A and 12B, the retrieval device 704 is configured to retrieve a device 800 having a stent 802 with a tip connector 808 comprising a hooked configuration. Accordingly, for example, the attachment portion 714 of the retrieval device 704 may comprise a lace component or wire shaped into a looped configuration. Alternatively, in the embodiment of FIG. 12C, the retrieval device 704 comprises an elongated catheter having an attachment portion 714 that defines a cavity with female threads disposed therein (i.e. a screw hole) and a magnet 716, while the tip connector 808 of the stent 802/807 of the device 800 comprises a corresponding portion having male screw threads (i.e. a screw tip) and a magnet 718 having a polarity that is attractive to magnet 716 of the retrieval device 704. Accordingly, in each of the aforementioned embodiments, a stent 802/807 of the device 800 that comprises a tip connector 808 may be easily engaged by the attachment portion 714 of the retrieval device 704.

In an exemplary method of application for the system 1000, the system 1000 may be used to retrieve a device 800 positioned within an aortic arch 104. For example, the device 800 may be positioned such that a first stent 802 or 807 of the device 800 is deployed within the left subclavian artery 118 and a second stent 802 of the device 800 is deployed within the right subclavian artery 120 or the innominate artery 114. The method comprises the step of percutaneously inserting a retrieval device 704 slidably disposed within a sleeve catheter 702 into a right radial or brachial artery and advancing the open distal end 708 of the sleeve catheter 702 to a location adjacent to one of the stents 802 or 807 (as applicable) of the deployed device 800. The retrieval device 704 is then advanced through the open distal end 708 of the sleeve catheter 702 such that the attachment portion 714 of the retrieval device 704 can engage the tip connector 808 of the stent 802/807. After the attachment portion 714 of the retrieval device 704 is securely coupled with a tip connector 808 of a stent 802/807 of the device 800, a user/operator can manipulate the proximal end (not shown) of the retrieval device 704 and thus manipulate the device 800. In this manner, a user/operation may move the stents 802/807 of a device 800 to their collapsed positions and thus disengage the device 800 from the aortic and/or arterial walls.

In the embodiment of the system 1000 shown in FIGS. 12A-12C, moving the stents 802/807 of the device 800 from their expanded/anchored position to their collapsed/disengaged position is accomplished by pulling the distal end 708 of the retrieval device 704 toward the proximal end 710 of the sleeve catheter 702, thereby applying pressure to the tip connector 808 of the stent 802/807. Moving the retrieval device 704 in the proximal direction applies pressure to the tip connector 808 of the stent 802/807, which translates to the extension portion 803 of the stent 802/807 and causes it to move from the expanded position to the collapsed position and disengaged from the aortic and/or arterial walls. Additionally, due to the linked configuration of the device 800, this pressure is also translated to any remaining stents 802/807 of the device 800, thereby disengaging and collapsing the same in a similar manner. After the stents 802/807 of the device 800 are disengaged, the retrieval device 704 (and thus the collapsed device 800 attached thereto) is retracted into the lumen 712 of the sleeve catheter 702 and slidably removed from the sleeve catheter 702 and the patient's body as shown in FIG. 12C.

The various devices, systems, and methods for preventing stroke of the present disclosure have various benefits to patients with various diseases and/or disorders of the heart and/or circulatory system. For example, patients with chronic atrial fibrillation (non-valvular atrial fibrillation), recurrence transient ischemic attack, atrial fibrillation and anticoagulation contraindications, and/or left atrial appendage thrombosis may have their risk of stroke either reduced or eliminated by way of an exemplary devices, systems, and/or method of the present disclosure. In addition, patients with acute myocardial infarct with left ventricular thrombus, atrial flutter (ablation and pulmonary vein isolation), cardiomyopathy with left ventricular enlargement, non-obstructive thrombus of a mechanical heart valve, patent foramen ovale (cryptogenic ischemic stroke) and/or an acute infection endocardiatis with valve vegetation without valve insufficiency under medical treatment (vegetation>1 cm which currently oblige to surgical remotion) may also benefit from the present disclosure.

Furthermore, it is noted that the various devices, systems, and methods for preventing stroke of the present disclosure have advantages as compared to anticoagulant and antiplatelet therapies, as not all patients are suitable for such therapies (given the high risk of bleeding, for example), and the relative cost of such therapies, which would be substantially higher as compared to the devices and systems as referenced herein. The various devices and systems would be useful for various aortic arch configurations, noting that there is diversity among arches.

While various embodiments of devices, systems, and methods for the prevention of stroke have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device for the prevention of stroke, the device comprising:
    a first stent and a second stent, each of the first stent and the second stent comprising an extension portion having a first end and a second end and sized and shaped to fit within at least part of an artery extending from an aortic arch; and
    a first deflection component and a second deflection component, each of the first and second deflection components comprising a frame and two or more parallel convex struts, the frame defining an interior and the two or more parallel convex struts positioned across the interior of the frame and configured to divert an embolus from entering the artery when the deflection component is positioned at or near the ostium of the artery;
    wherein the second end of the first stent is coupled with the first deflection component, the first deflection component is positioned between the first stent and the second deflection component, the frame defining an interior of the second deflection component is configured to be substantially the same size or larger than an ostium of an artery extending from the aortic arch, the second stent does not comprise a deflection component or other structure configured to divert an embolus from entering the artery when the second stent is positioned within the artery, the first deflection component is coupled with the second deflection component by a first set of one or more connecting wires and the second stent is coupled with the second deflection component by a second set of one or more connecting wires.

2. The device of claim 1, wherein:
    the frame of the first deflection component comprises the second end of the extension portion of the first stent and the interior of the first deflection component comprises an opening defined within the second end of the extension portion of the first stent; and
    the second deflection component is coupled with the first deflection component and the second stent by the first set of one or more connecting wires.

3. The device of claim 1, wherein:
    the first deflection component is coupled with the first stent by a third set of one or more connecting wires.

4. The device of claim 1, wherein the first deflection component and a second deflection component are configured as a unit, the unit configured to conform to the curvature of the aortic arch and coupled with the first stent by the first set of one or more connection wires and the second stent by the second set of one or more connecting wires.

5. The device of claim 1, wherein the two or more parallel convex struts of each of the first and second deflection components comprise four or more parallel convex struts.

6. The device of claim 1, wherein the two or more parallel convex struts of each of the first and second deflection components are positioned between about 0.75 mm to about 1.0 mm, inclusive, from one another.

7. The device of claim 1, wherein when the device is positioned within the aortic arch, the two or more parallel convex struts of each of the first and second deflection components are positioned in an orientation that is approximately perpendicular to, or in an oblique manner relative to, a direction of blood flow within the aortic arch.

8. The device of claim 1, wherein when the device is positioned within the aortic arch, the two or more parallel convex struts of each of the first and second deflection components are positioned in an orientation that is approximately parallel with a direction of blood flow within the aortic arch.

9. The device of claim 1, wherein the diameter of each of the two or more parallel convex struts of each of the first and second deflection components is between about 0.25 mm to about 1.0 mm, inclusive.

10. The device of claim 1, wherein the at least one of the first and second sets of one or more connecting wires comprise springs.

11. The device of claim 1, wherein at least one of the first stent and the second stent further comprises an anchor portion coupled with the second end of the extension portion, the anchor portion sized and shaped to prevent the stent from advancing into the artery extending from the aortic arch in which the extension portion may be at least partially positioned.

12. The device of claim 11, wherein the anchor portion comprises either a flange portion or two or more wings.

13. The device of claim 1, wherein the first and second stents are each autoexpandable from a collapsed configuration to an expanded configuration and the first end of the extension portion of each of the first and second stents further comprises a tip connector configured to facilitate moving each stent from the expanded configuration to the collapsed configuration.

14. The device of claim 1, further comprising one or more radiopaque markers positioned thereon.

15. A retrieval system for the prevention of stroke, the system comprising:
 a device for the prevention of a stroke, the device comprising:
  a first stent and a second stent, each of the first stent and the second stent comprising an extension portion having a first end and a second end, the extension portion sized and shaped to fit within at least part of an artery extending from an aortic arch and the first end of at least one of the extension portions of the first and second stents comprising a tip connector, and
  a first deflection component and a second deflection component, each of the first and second deflection components comprising a frame and two or more parallel convex struts, the frame defining an interior and the two or more parallel convex struts positioned across the interior of the frame and configured to divert an embolus from entering the artery when the deflection component is positioned at or near the ostium of the artery,
  wherein the second end of the first stent is coupled with the first deflection component, the first deflection component is positioned between the first stent and the second deflection component, the frame defining an interior of the second deflection component is configured to be substantially the same size or larger than an ostium of an artery extending from the aortic arch, the second stent does not comprise a deflection component or other structure configured to divert an embolus from entering the artery when the second stent is positioned within the artery, the first deflection component is coupled with the second deflection component by a first set of one or more connecting wires and the second stent is coupled with the second deflection component by a second set of one or more connecting wires;
 a sleeve catheter configured for intravascular insertion and advancement, the sleeve catheter comprising a proximal end, an open distal end, and a lumen extending therebetween; and
 a retrieval device slidably disposed within the lumen of the sleeve catheter, the retrieval device comprising a proximal end for manipulation by a user and a distal end comprising an attachment portion configured to engage the tip connector of the extension portion of the first and/or second stents.

16. The retrieval system of claim 15 wherein:
 the frame of the first deflection component comprises the second end of the extension portion of the first stent and the interior of the first deflection component comprises an opening defined within the second end of the extension portion of the first stent; and
 the second deflection component is coupled with the first deflection component and the second stent by the first set of one or more connecting wires.

17. The retrieval device of claim 15, wherein:
 the tip connector comprises a screw tip and a first magnet and the attachment portion of the retrieval device comprises a screw hole and a second magnet; and
 the screw tip and the first magnet are configured to securely engage the screw hole and the second magnet, respectively.

18. The retrieval device of claim 15, wherein the attachment portion of the retrieval device comprises a lace component and the tip connector comprises a hook tip configured to engage the lace component of the retrieval device.

19. A method for preventing stroke, the method comprising the steps of:
 introducing a device for preventing stroke into a body, the device comprising:
  at least two stents, each stent comprising an extension portion having a first end and a second end, the extension portion sized and shaped to fit within at least part of an artery extending from an aortic arch, and
  at least one deflection component comprising a frame and two or more parallel convex struts, the frame defining an interior and the two or more parallel convex struts positioned across the interior and configured to divert an embolus from entering the artery when the deflection component is positioned at or near the ostium of the artery,
  wherein at least one of the stents is coupled with the at least one deflection component by one or more connecting wires;
 navigating the device within the body until the device reaches an aortic arch;
 positioning a first stent within a first vessel branching from the aortic arch so that each of the at least one deflection components substantially covers an ostium of a vessel branching from the aortic arch;
 anchoring the first stent within the first vessel by deploying the extension portion of the first stent;
 positioning a second stent within a second vessel branching from the aortic arch;
 anchoring the second stent within the second vessel by deploying the extension portion of the second stent;
 introducing a retrieval system into a body, the retrieval system comprising:
  a sleeve catheter configured for intravascular insertion and advancement and comprising a proximal end, an open distal end, a lumen extending therebetween, and
  a retrieval device slidably disposed within the lumen of the sleeve catheter and comprising a proximal end for manipulation by a user and a distal end comprising an attachment portion configured to engage a tip connector of at least one of the extension portions of the stents;
 navigating the sleeve catheter within the body until the open distal end of the sleeve catheter reaches the second vessel branching from the aortic arch;
 advancing the distal end of the retrieval catheter through the open distal end of the sleeve catheter so that the attachment portion of the retrieval catheter engages a tip connector on the first end of the extension portion of the second stent;
 disengaging the second stent from the second vessel;
 disengaging the first stent from the first vessel; and
 withdrawing the device and the retrieval system from the body.

20. The method of claim 19, wherein:
the at least two stents of the device for preventing stroke comprises a first stent for placement within the first vessel branching from the aortic arch and a second stent for placement within the second vessel extending from the aortic arch;
the at least one deflection component comprises a first deflection component and a second deflection component; and
the one or more connecting wires comprises a first set of one or more connection wires and a second set of one or more connecting wires;
wherein the second end of the first stent is coupled with the first deflection component, the first deflection component is positioned between the first stent and the second deflection component, the frame defining an interior of the second deflection component is configured to be substantially the same size or larger than an ostium of an artery extending from the aortic arch, the second stent does not comprise a deflection component or other structure configured to divert an embolus from entering the second vessel in which the second stent is positioned, the first deflection component is coupled with the second deflection component by the first set of one or more connecting wires and the second stent is coupled with the second deflection component by the second set of one or more connecting wires.

* * * * *